US008801186B2

(12) United States Patent
Frey et al.

(10) Patent No.: US 8,801,186 B2
(45) Date of Patent: Aug. 12, 2014

(54) SYSTEM AND METHOD OF SCAN CONTROLLED ILLUMINATION OF STRUCTURES WITHIN AN EYE

(75) Inventors: Rudolph W. Frey, Winter Park, FL (US); Richard Ty Olmstead, Oviedo, FL (US); Gary P. Gray, Orlando, FL (US); Steven E. Bott, Oviedo, FL (US); James Strobel, Titusville, FL (US)

(73) Assignee: LensAR, Inc., Orlando, FL (US)

( * ) Notice: Subject to any disclaimer, the term of this patent is extended or adjusted under 35 U.S.C. 154(b) by 148 days.

(21) Appl. No.: 13/273,653

(22) Filed: Oct. 14, 2011

(65) Prior Publication Data

US 2012/0182522 A1 Jul. 19, 2012

Related U.S. Application Data

(60) Provisional application No. 61/455,178, filed on Oct. 15, 2010.

(51) Int. Cl.
*A61B 3/10* (2006.01)
*A61B 3/107* (2006.01)
*A61B 3/117* (2006.01)

(52) U.S. Cl.
CPC ............. *A61B 3/008* (2013.01); *A61B 3/107* (2013.01); *A61B 3/1173* (2013.01)
USPC ............ 351/221; 351/210; 351/212; 351/246

(58) Field of Classification Search
CPC ..... A61B 3/0008; A61B 3/107; A61B 3/1173
USPC .......................... 351/205, 210, 212, 221, 246
See application file for complete search history.

(56) References Cited

U.S. PATENT DOCUMENTS

| | | |
|---|---|---|
| 3,074,407 A | 1/1963 | Moon et al. |
| 3,971,382 A | 7/1976 | Krasnov |
| 3,982,541 A | 9/1976 | L'Esperance, Jr. |
| 4,024,852 A | 5/1977 | L'Esperance et al. |
| 4,263,893 A | 4/1981 | Pavlak et al. |
| 4,306,546 A | 12/1981 | Heine et al. |
| 4,309,998 A | 1/1982 | Aron nee Rosa et al. |
| 4,334,736 A | 6/1982 | Herbert |
| 4,381,007 A | 4/1983 | Doss |
| 4,394,144 A | 7/1983 | Aoki |
| 4,403,841 A | 9/1983 | Lang et al. |

(Continued)

FOREIGN PATENT DOCUMENTS

| | | |
|---|---|---|
| CA | 2553963 A1 | 8/2005 |
| CA | 2680072 A1 | 9/2008 |

(Continued)

OTHER PUBLICATIONS

U.S. Appl. No. 11/337,127, filed Jan. 20, 2006, Frey et al.

(Continued)

*Primary Examiner* — Huy K Mai
(74) *Attorney, Agent, or Firm* — Brinks Gilson & Lione

(57) ABSTRACT

There is provided a system, apparatus and methods for enhancing the illumination of structures of the eye using predetermined scan patterns of an illuminating light beam. The systems, apparatus and methods further provide for obtaining enhanced single images of multiple structures of the eye.

9 Claims, 8 Drawing Sheets

(56) References Cited

U.S. PATENT DOCUMENTS

| | | |
|---|---|---|
| 4,461,294 A | 7/1984 | Baron |
| 4,477,159 A | 10/1984 | Mizuno et al. |
| 4,502,816 A | 3/1985 | Creter, Jr. et al. |
| 4,517,980 A | 5/1985 | Tagnon |
| 4,537,193 A | 8/1985 | Tanner |
| 4,538,608 A | 9/1985 | L'Esperance, Jr. |
| 4,554,917 A | 11/1985 | Tagnon |
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch et al. |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Schroder et al. |
| 4,702,576 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Weinberg |
| 4,721,379 A | 1/1988 | L'Esperance |
| 4,724,522 A | 2/1988 | Belgorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,741,612 A | 5/1988 | Birngruber et al. |
| 4,744,362 A | 5/1988 | Gründler |
| 4,758,081 A | 7/1988 | Barnes |
| 4,765,336 A | 8/1988 | Blaha et al. |
| 4,770,162 A | 9/1988 | L'Esperance et al. |
| 4,770,172 A | 9/1988 | L'Esperance, Jr. |
| 4,770,486 A | 9/1988 | Wang et al. |
| 4,772,116 A | 9/1988 | Schroder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,884,884 A | 12/1989 | Reis |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiyama |
| 4,901,718 A | 2/1990 | Bille et al. |
| 4,902,124 A | 2/1990 | Roy, Sr. et al. |
| 4,903,695 A | 2/1990 | Warner et al. |
| 4,905,711 A | 3/1990 | Bennett et al. |
| 4,907,586 A | 3/1990 | Bille et al. |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance, Jr. |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell, Jr. et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,054,907 A | 10/1991 | Sklar et al. |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,094,521 A | 3/1992 | Jolson et al. |
| 5,098,426 A | 3/1992 | Sklar et al. |
| 5,102,409 A | 4/1992 | Balgorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance, III et al. |
| 5,152,759 A | 10/1992 | Parel et al. |
| 5,163,934 A | 11/1992 | Munnerlyn |
| 5,171,242 A | 12/1992 | Dewey et al. |
| 5,174,021 A | 12/1992 | L'Esperance, III et al. |
| 5,178,635 A | 1/1993 | Gwon et al. |
| 5,188,631 A | 2/1993 | L'Esperance, Jr. |
| 5,194,948 A | 3/1993 | L'Esperance, III et al. |
| 5,196,006 A | 3/1993 | Klopotek et al. |
| 5,196,027 A | 3/1993 | Thompson et al. |
| 5,201,730 A | 4/1993 | Easley et al. |
| 5,202,708 A | 4/1993 | Sasaki et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Bille et al. |
| 5,246,436 A | 9/1993 | Rowe |
| 5,257,988 A | 11/1993 | L'Esperance, Jr. |
| 5,258,025 A | 11/1993 | Fedorov et al. |

(56) References Cited

U.S. PATENT DOCUMENTS

| | | |
|---|---|---|
| 5,263,950 A | 11/1993 | L'Esperance, Jr. |
| 5,263,951 A | 11/1993 | Spears et al. |
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |
| 5,282,798 A | 2/1994 | Bruse et al. |
| 5,284,477 A | 2/1994 | Hanna et al. |
| 5,288,293 A | 2/1994 | O'Donnell, Jr. |
| 5,290,272 A | 3/1994 | Burstein et al. |
| 5,295,989 A | 3/1994 | Nakamura |
| 5,300,020 A | 4/1994 | L'Esperance, Jr. |
| 5,300,061 A | 4/1994 | Easley et al. |
| 5,300,062 A | 4/1994 | Ueno |
| 5,300,063 A | 4/1994 | Tano et al. |
| 5,300,114 A | 4/1994 | Gwon et al. |
| 5,304,168 A | 4/1994 | Sun |
| 5,304,169 A | 4/1994 | Sand |
| 5,311,224 A | 5/1994 | Enomoto |
| 5,312,320 A | 5/1994 | L'Esperance, Jr. |
| 5,312,393 A | 5/1994 | Mastel |
| 5,314,422 A | 5/1994 | Nizzola |
| 5,318,047 A | 6/1994 | Davenport et al. |
| 5,318,560 A | 6/1994 | Blount et al. |
| 5,323,788 A | 6/1994 | Silvestrini et al. |
| 5,324,281 A | 6/1994 | Muller |
| 5,325,134 A | 6/1994 | Kohayakawa |
| 5,334,190 A | 8/1994 | Seiler |
| 5,336,215 A | 8/1994 | Hsueh et al. |
| 5,336,216 A | 8/1994 | Dewey |
| 5,342,351 A | 8/1994 | Blaha et al. |
| 5,342,370 A | 8/1994 | Simon et al. |
| 5,345,948 A | 9/1994 | O'Donnell, Jr. |
| 5,346,491 A | 9/1994 | Oertli |
| 5,347,329 A | 9/1994 | Ota |
| 5,348,551 A | 9/1994 | Spears et al. |
| 5,350,374 A | 9/1994 | Smith |
| 5,354,331 A | 10/1994 | Schachar |
| 5,355,181 A | 10/1994 | Ashizaki et al. |
| 5,356,407 A | 10/1994 | Easley et al. |
| 5,356,409 A | 10/1994 | Nizzola |
| 5,360,424 A | 11/1994 | Klopotek |
| 5,364,388 A | 11/1994 | Koziol |
| 5,364,390 A | 11/1994 | Taboada et al. |
| 5,368,590 A | 11/1994 | Itoh |
| 5,370,641 A | 12/1994 | O'Donnell, Jr. |
| 5,372,595 A | 12/1994 | Gaasterland et al. |
| 5,374,265 A | 12/1994 | Sand |
| 5,376,086 A | 12/1994 | Khoobehi et al. |
| 5,391,165 A | 2/1995 | Fountain et al. |
| 5,395,356 A | 3/1995 | King et al. |
| 5,403,307 A | 4/1995 | Zelman |
| 5,408,484 A | 4/1995 | Weimel |
| 5,411,501 A | 5/1995 | Klopotek |
| 5,412,561 A | 5/1995 | Rosenshein et al. |
| 5,413,555 A | 5/1995 | McMahan |
| 5,423,798 A | 6/1995 | Crow |
| 5,423,800 A | 6/1995 | Ren et al. |
| 5,423,801 A | 6/1995 | Marshall et al. |
| 5,425,727 A | 6/1995 | Koziol |
| 5,425,729 A | 6/1995 | Ishida et al. |
| 5,425,730 A | 6/1995 | Luloh |
| 5,437,657 A | 8/1995 | Epstein |
| 5,437,658 A | 8/1995 | Muller et al. |
| 5,439,462 A | 8/1995 | Bille et al. |
| 5,441,496 A | 8/1995 | Easley et al. |
| 5,441,511 A | 8/1995 | Hanna |
| 5,442,412 A | 8/1995 | Frey et al. |
| 5,442,487 A | 8/1995 | Mizuno |
| 5,445,633 A | 8/1995 | Nakamura et al. |
| 5,460,627 A | 10/1995 | O'Donnell, Jr. |
| 5,461,212 A | 10/1995 | Seiler et al. |
| 5,462,739 A | 10/1995 | Dan et al. |
| 5,465,737 A | 11/1995 | Schachar |
| 5,470,329 A | 11/1995 | Sumiya |
| 5,474,548 A | 12/1995 | Knopp et al. |
| 5,476,511 A | 12/1995 | Gwon et al. |
| 5,480,396 A | 1/1996 | Simon et al. |
| 5,484,432 A | 1/1996 | Sand |
| 5,489,299 A | 2/1996 | Schachar |
| 5,503,165 A | 4/1996 | Schachar |
| 5,507,740 A | 4/1996 | O'Donnell, Jr. |
| 5,514,124 A | 5/1996 | Alpins |
| 5,514,125 A | 5/1996 | Lasser et al. |
| 5,520,679 A | 5/1996 | Lin |
| 5,527,774 A | 6/1996 | Girard |
| 5,529,076 A | 6/1996 | Schachar |
| 5,531,753 A | 7/1996 | Oliveira |
| 5,533,997 A | 7/1996 | Ruiz |
| 5,548,352 A | 8/1996 | Dewey |
| 5,549,632 A | 8/1996 | Lai |
| 5,556,395 A | 9/1996 | Shimmick et al. |
| 5,573,544 A | 11/1996 | Simon et al. |
| 5,594,753 A | 1/1997 | Frey et al. |
| 5,607,472 A | 3/1997 | Thompson |
| 5,616,139 A | 4/1997 | Okamoto |
| 5,618,284 A | 4/1997 | Sand |
| 5,620,435 A | 4/1997 | Belkin et al. |
| 5,627,162 A | 5/1997 | Gwon et al. |
| 5,632,742 A | 5/1997 | Frey et al. |
| 5,651,782 A | 7/1997 | Simon et al. |
| 5,656,186 A | 8/1997 | Mourou et al. |
| 5,684,560 A | 11/1997 | Roffman et al. |
| 5,699,142 A | 12/1997 | Lee et al. |
| 5,709,868 A | 1/1998 | Perricone |
| 5,722,952 A | 3/1998 | Schachar |
| 5,722,970 A | 3/1998 | Colvard et al. |
| 5,731,909 A | 3/1998 | Schachar |
| 5,738,677 A | 4/1998 | Colvard et al. |
| 5,752,950 A | 5/1998 | Frey et al. |
| 5,757,462 A | 5/1998 | Nanjo |
| 5,766,171 A | 6/1998 | Silvestrini |
| 5,773,472 A | 6/1998 | Stjernschantz et al. |
| 5,828,686 A | 10/1998 | Frey et al. |
| 5,843,184 A | 12/1998 | Cionni |
| 5,849,006 A | 12/1998 | Frey et al. |
| 5,886,768 A | 3/1999 | Knopp et al. |
| 5,907,908 A | 6/1999 | Cunanan et al. |
| 5,912,915 A | 6/1999 | Reed et al. |
| 5,919,186 A | 7/1999 | Bath |
| 5,928,129 A | 7/1999 | Ruiz |
| 5,980,513 A | 11/1999 | Frey et al. |
| 5,984,916 A | 11/1999 | Lai |
| 5,993,441 A | 11/1999 | Muller et al. |
| 6,007,578 A | 12/1999 | Schachar |
| 6,013,101 A | 1/2000 | Israel |
| 6,019,472 A | 2/2000 | Koester et al. |
| 6,022,088 A | 2/2000 | Metzler |
| 6,027,494 A | 2/2000 | Frey |
| 6,055,259 A | 4/2000 | Frey et al. |
| 6,059,772 A | 5/2000 | Hsia et al. |
| 6,070,981 A | 6/2000 | Mihashi et al. |
| 6,099,522 A | 8/2000 | Knopp et al. |
| 6,114,651 A | 9/2000 | Schluter et al. |
| 6,132,424 A | 10/2000 | Tang |
| 6,186,148 B1 | 2/2001 | Okada |
| 6,190,375 B1 | 2/2001 | Frey |
| 6,197,018 B1 | 3/2001 | O'Donnell |
| 6,197,056 B1 | 3/2001 | Schachar |
| 6,252,595 B1 | 6/2001 | Birmingham et al. |
| 6,254,595 B1 | 7/2001 | Juhasz et al. |
| 6,261,220 B1 | 7/2001 | Frey et al. |
| 6,271,914 B1 | 8/2001 | Frey et al. |
| 6,271,915 B1 | 8/2001 | Frey et al. |
| 6,275,718 B1 | 8/2001 | Lempert |
| 6,280,435 B1 | 8/2001 | Odrich et al. |
| 6,280,468 B1 | 8/2001 | Schachar |
| 6,299,640 B1 | 10/2001 | Schachar |
| 6,302,879 B1 | 10/2001 | Frey et al. |
| 6,312,422 B1 | 11/2001 | Dubnack |
| 6,312,424 B1 | 11/2001 | Largent |
| 6,313,165 B1 | 11/2001 | Grunberger et al. |
| 6,315,773 B1 | 11/2001 | Frey et al. |

(56) References Cited

U.S. PATENT DOCUMENTS

| | | |
|---|---|---|
| 6,319,274 B1 | 11/2001 | Shadduck |
| 6,322,545 B1 | 11/2001 | Schachar |
| 6,322,556 B1 | 11/2001 | Gwon et al. |
| 6,324,191 B1 | 11/2001 | Horvath |
| 6,325,791 B1 | 12/2001 | Shimoji |
| 6,325,792 B1 | 12/2001 | Swinger et al. |
| 6,328,732 B1 | 12/2001 | Donitzky et al. |
| 6,344,040 B1 | 2/2002 | Juhasz et al. |
| 6,373,571 B1 | 4/2002 | Juhasz et al. |
| D459,806 S | 7/2002 | Webb |
| D459,807 S | 7/2002 | Webb |
| 6,413,262 B2 | 7/2002 | Saishin et al. |
| D462,442 S | 9/2002 | Webb |
| D462,443 S | 9/2002 | Webb |
| 6,451,008 B1 | 9/2002 | Frey et al. |
| 6,460,997 B1 | 10/2002 | Frey et al. |
| 6,467,906 B1 | 10/2002 | Alpins |
| 6,493,151 B2 | 12/2002 | Schachar |
| 6,494,910 B1 | 12/2002 | Ganem et al. |
| 6,497,483 B2 | 12/2002 | Frey et al. |
| 6,530,917 B1 | 3/2003 | Seiler et al. |
| 6,544,254 B1 | 4/2003 | Bath |
| 6,547,394 B2 | 4/2003 | Doherty |
| 6,554,825 B1 | 4/2003 | Murray et al. |
| 6,585,726 B2 | 7/2003 | Frey et al. |
| 6,588,902 B2 | 7/2003 | Isogai |
| 6,588,903 B2 | 7/2003 | Rathjen |
| 6,592,574 B1 | 7/2003 | Shimmick et al. |
| 6,610,686 B1 | 8/2003 | Enrico et al. |
| 6,623,476 B2 | 9/2003 | Juhasz et al. |
| 6,626,445 B2 | 9/2003 | Murphy et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Lieberman et al. |
| 6,676,653 B2 | 1/2004 | Juhasz et al. |
| 6,693,927 B1 | 2/2004 | Horvath et al. |
| 6,726,679 B1 | 4/2004 | Dick et al. |
| 6,849,091 B1 | 2/2005 | Cumming |
| 6,863,667 B2 | 3/2005 | Webb et al. |
| 6,905,641 B2 | 6/2005 | Platt et al. |
| 6,923,955 B2 | 8/2005 | Till et al. |
| 6,962,583 B2 | 11/2005 | Kadziauskas et al. |
| 7,044,568 B2 | 5/2006 | Olivera et al. |
| 7,077,838 B2 | 7/2006 | Wong |
| 7,182,759 B2 | 2/2007 | Kadziauskas et al. |
| 7,188,949 B2 | 3/2007 | Bandhauer et al. |
| 7,220,255 B2 | 5/2007 | Lai |
| 7,252,662 B2 | 8/2007 | McArdle et al. |
| 7,264,355 B2 | 9/2007 | Rathjen |
| RE40,002 E | 1/2008 | Lin |
| RE40,184 E | 3/2008 | Lin |
| 7,338,167 B2 | 3/2008 | Zelvin et al. |
| 7,357,504 B2 | 4/2008 | Fischer et al. |
| 7,364,575 B2 | 4/2008 | Van Saarloos |
| 7,390,089 B2 | 6/2008 | Loesel et al. |
| RE40,420 E | 7/2008 | Dick et al. |
| 7,402,159 B2 | 7/2008 | Loesel et al. |
| 7,467,871 B2 | 12/2008 | Lawhorn et al. |
| 7,479,106 B2 | 1/2009 | Banik et al. |
| 7,540,613 B2 | 6/2009 | Severns |
| 7,655,002 B2 | 2/2010 | Myers |
| 7,717,908 B2 | 5/2010 | Ruiz et al. |
| 7,766,903 B2 | 8/2010 | Blumenkranz et al. |
| 7,836,894 B2 | 11/2010 | Brinkmann et al. |
| 7,959,289 B2 | 6/2011 | Cattin-Liebl |
| 8,262,553 B2 | 9/2012 | Weston et al. |
| 8,262,646 B2 | 9/2012 | Frey et al. |
| 8,382,745 B2 | 2/2013 | Naranjo-Tackman et al. |
| 8,465,478 B2 | 6/2013 | Frey et al. |
| 8,475,433 B2 | 7/2013 | Mrochen et al. |
| 8,480,659 B2 | 7/2013 | Frey et al. |
| 8,500,723 B2 | 8/2013 | Frey et al. |
| 8,556,425 B2 | 10/2013 | Frey et al. |
| D694,890 S | 12/2013 | Bott et al. |
| D695,408 S | 12/2013 | Bott et al. |
| 8,617,146 B2 | 12/2013 | Naranjo-Tackman et al. |
| 2001/0029363 A1 | 10/2001 | Lin |
| 2002/0004658 A1 | 1/2002 | Munnerlyn et al. |
| 2002/0025311 A1 | 2/2002 | Till |
| 2002/0029053 A1 | 3/2002 | Gordon |
| 2002/0049437 A1 | 4/2002 | Silvestrini |
| 2002/0049450 A1 | 4/2002 | Myers |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2002/0159028 A1 | 10/2002 | Masaki |
| 2003/0050629 A1 | 3/2003 | Kadziauskas et al. |
| 2003/0055412 A1 | 3/2003 | Lieberman et al. |
| 2003/0076477 A1 | 4/2003 | Matsumoto |
| 2003/0076508 A1 | 4/2003 | Cornsweet |
| 2003/0109926 A1 | 6/2003 | Portney |
| 2003/0135272 A1 | 7/2003 | Brady et al. |
| 2003/0139737 A1 | 7/2003 | Lin |
| 2003/0212387 A1 | 11/2003 | Kurtz et al. |
| 2003/0220630 A1 | 11/2003 | Lin et al. |
| 2003/0236515 A1 | 12/2003 | Lieberman et al. |
| 2004/0054359 A1 | 3/2004 | Ruiz et al. |
| 2004/0059321 A1 | 3/2004 | Knopp et al. |
| 2004/0070761 A1 | 4/2004 | Horvath et al. |
| 2004/0106929 A1 | 6/2004 | Masket |
| 2004/0143244 A1 | 7/2004 | Gray et al. |
| 2004/0156014 A1 | 8/2004 | Piers et al. |
| 2004/0199149 A1 | 10/2004 | Myers et al. |
| 2004/0199150 A1 | 10/2004 | Lai |
| 2004/0243111 A1 | 12/2004 | Bendett et al. |
| 2004/0249403 A1 | 12/2004 | Loomas et al. |
| 2005/0107773 A1 | 5/2005 | Bergt et al. |
| 2005/0107775 A1 | 5/2005 | Huang et al. |
| 2005/0165387 A1 | 7/2005 | Lubatschowski et al. |
| 2005/0197655 A1 | 9/2005 | Telfair et al. |
| 2005/0203492 A1 | 9/2005 | Nguyen et al. |
| 2005/0241653 A1 | 11/2005 | Van Heugten et al. |
| 2005/0243276 A1 | 11/2005 | Van Heugten et al. |
| 2005/0270486 A1 | 12/2005 | Teiwes et al. |
| 2005/0286019 A1 | 12/2005 | Wiltberger et al. |
| 2006/0058682 A1 | 3/2006 | Miller et al. |
| 2006/0192921 A1 | 8/2006 | Loesel et al. |
| 2006/0195076 A1 | 8/2006 | Blumenkranz et al. |
| 2006/0215111 A1 | 9/2006 | Mihashi |
| 2006/0217688 A1 | 9/2006 | Lai |
| 2006/0259022 A1 | 11/2006 | Lin |
| 2007/0010803 A1 | 1/2007 | Bischoff et al. |
| 2007/0078447 A1 | 4/2007 | Weinacht et al. |
| 2007/0093795 A1 | 4/2007 | Melcher et al. |
| 2007/0093796 A1 | 4/2007 | Raksi et al. |
| 2007/0129693 A1 | 6/2007 | Hunter et al. |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0265603 A1 | 11/2007 | Pinelli |
| 2008/0058841 A1 | 3/2008 | Kurtz et al. |
| 2008/0071254 A1 | 3/2008 | Lummis et al. |
| 2008/0077121 A1 | 3/2008 | Rathjen |
| 2008/0111972 A1 | 5/2008 | Barth et al. |
| 2008/0114386 A1 | 5/2008 | Iliakis et al. |
| 2008/0186551 A1 | 8/2008 | Hanft et al. |
| 2008/0275433 A1 | 11/2008 | Russmann et al. |
| 2008/0281303 A1 | 11/2008 | Culbertson et al. |
| 2008/0312675 A1 | 12/2008 | Newcott et al. |
| 2009/0012507 A1 | 1/2009 | Culbertson et al. |
| 2009/0069794 A1 | 3/2009 | Kurtz |
| 2009/0088734 A1 | 4/2009 | Mordaunt |
| 2009/0126870 A1 | 5/2009 | Zadoyan et al. |
| 2009/0131921 A1 | 5/2009 | Kurtz |
| 2009/0137988 A1 | 5/2009 | Kurtz |
| 2009/0137991 A1 | 5/2009 | Kurtz |
| 2009/0137993 A1 | 5/2009 | Kurtz |
| 2009/0157063 A1 | 6/2009 | Ruiz et al. |

(56) References Cited

U.S. PATENT DOCUMENTS

| | | | |
|---|---|---|---|
| 2009/0161065 A1 | 6/2009 | Smith, III et al. |
| 2009/0171327 A1 | 7/2009 | Kurtz et al. |
| 2009/0177189 A1 | 7/2009 | Raksi |
| 2009/0187178 A1 | 7/2009 | Muller et al. |
| 2009/0192389 A1 | 7/2009 | Eilers et al. |
| 2009/0209954 A1 | 8/2009 | Muller et al. |
| 2009/0244482 A1 | 10/2009 | Elsner et al. |
| 2009/0281530 A1 | 11/2009 | Korn |
| 2009/0287232 A1 | 11/2009 | Davis |
| 2010/0002837 A1 | 1/2010 | Gertner et al. |
| 2010/0004641 A1 | 1/2010 | Frey et al. |
| 2010/0004643 A1 | 1/2010 | Frey et al. |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0060855 A1 | 3/2010 | Graether |
| 2010/0114079 A1 | 5/2010 | Myers et al. |
| 2010/0249761 A1 | 9/2010 | Ruiz et al. |
| 2010/0256614 A1 | 10/2010 | Donitzky et al. |
| 2010/0256615 A1 | 10/2010 | Blumenkranz et al. |
| 2010/0274228 A1 | 10/2010 | Mrochen et al. |
| 2010/0292676 A1 | 11/2010 | Larsen |
| 2010/0292678 A1 | 11/2010 | Frey et al. |
| 2010/0312231 A1 | 12/2010 | Singh |
| 2010/0324542 A1 | 12/2010 | Kurtz |
| 2010/0331829 A1 | 12/2010 | Bor et al. |
| 2011/0022035 A1 | 1/2011 | Porter et al. |
| 2011/0022036 A1 | 1/2011 | Frey et al. |
| 2011/0028950 A1 | 2/2011 | Raksi et al. |
| 2011/0040293 A1 | 2/2011 | Bor |
| 2011/0092965 A1 | 4/2011 | Slatkine |
| 2011/0118712 A1 | 5/2011 | Lubatschowski et al. |
| 2011/0137301 A1 | 6/2011 | Bartoli |
| 2011/0149240 A1 | 6/2011 | Alpins |
| 2011/0160710 A1 | 6/2011 | Frey et al. |
| 2011/0160711 A1 | 6/2011 | Naranjo-Tackman et al. |
| 2011/0166557 A1 | 7/2011 | Naranjo-Tackman et al. |
| 2011/0172649 A1 | 7/2011 | Schuele et al. |
| 2011/0184395 A1 | 7/2011 | Schuele et al. |
| 2011/0187995 A1 | 8/2011 | Frey et al. |
| 2011/0190739 A1 | 8/2011 | Frey et al. |
| 2011/0190740 A1 | 8/2011 | Frey et al. |
| 2011/0292340 A1 | 12/2011 | Shimizu et al. |
| 2012/0016350 A1 | 1/2012 | Myers et al. |
| 2012/0089134 A1* | 4/2012 | Horvath et al. .................. 606/6 |
| 2012/0229767 A1 | 9/2012 | Alpins |
| 2012/0265181 A1 | 10/2012 | Frey |
| 2012/0271286 A1 | 10/2012 | Curatu et al. |
| 2012/0296321 A1 | 11/2012 | Frey et al. |
| 2012/0330290 A1 | 12/2012 | Gray et al. |
| 2013/0265542 A1 | 10/2013 | Frey et al. |

FOREIGN PATENT DOCUMENTS

| | | |
|---|---|---|
| DE | 10 2005 001 249 A1 | 7/2006 |
| EP | 0 397 962 A1 | 11/1990 |
| EP | 0 933 060 A1 | 8/1999 |
| EP | 1 970 034 A1 | 9/2008 |
| FR | 2 497 087 A1 | 7/1982 |
| JP | 5-115437 A | 5/1993 |
| WO | WO 91/19539 A1 | 12/1991 |
| WO | WO 01/13838 A1 | 3/2001 |
| WO | WO 03/002010 A1 | 1/2003 |
| WO | WO 2005/070358 A1 | 8/2005 |
| WO | WO 2006/074469 A1 | 7/2006 |
| WO | WO 2008/112292 A1 | 9/2008 |
| WO | WO 2008/150330 A1 | 12/2008 |
| WO | WO 2010/022745 A1 | 3/2010 |
| WO | WO 2012/051490 A1 | 4/2012 |

OTHER PUBLICATIONS

U.S. Appl. No. 11/414,819, filed May 1, 2006, Frey et al.
U.S. Appl. No. 12/217,285, filed Jul. 2, 2008, Frey et al.
U.S. Appl. No. 12/217,295, filed Jul. 2, 2008, Frey et al.
U.S. Appl. No. 12/509,021, filed Jul. 24, 2009, Frey et al.
U.S. Appl. No. 12/509,211, filed Jul. 24, 2009, Frey et al.
U.S. Appl. No. 12/509,412, filed Jul. 24, 2009, Frey et al.
U.S. Appl. No. 12/685,850, filed Jan. 12, 2010, Myers et al.
U.S. Appl. No. 12/831,845, filed Jul. 7, 2010, Naranjo-Tackman et al.
U.S. Appl. No. 12/831,859, filed Jul. 7, 2010, Naranjo-Tackman et al.
U.S. Appl. No. 12/831,783, filed Jul. 7, 2010, Frey et al.
U.S. Appl. No. 12/840,818, filed Jul. 21, 2010, Porter et al.
U.S. Appl. No. 12/842,870, filed Jul. 23, 2010, Frey et al.
U.S. Appl. No. 29/377,018, filed Oct. 15, 2010, Bott et al.
U.S. Appl. No. 29/377,054, filed Oct. 15, 2010, Bott et al.
U.S. Appl. No. 13/016,593, filed Jan. 28, 2010, Frey et al.
U.S. Appl. No. 13/017,499, filed Jan. 31, 2011, Frey et al.
U.S. Appl. No. 13/017,702, filed Jan. 31, 2011, Frey et al.
U.S. Appl. No. 13/243,406, filed Sep. 23, 2011, Myers et al.
U.S. Appl. No. 13/427,130, filed Mar. 22, 2012, Frey.
U.S. Appl. No. 13/427,149, filed Mar. 22, 2012, Frey et al.
FDA PMA P030002 titled "crystalens™ Model AT-45 Accomodating Posterior Chamber Intraocular Lens (OIO)", dated Nov. 14, 2003, 16 pgs.
FDA PMA P040020 titled "AcrySof® ResSTOR® Apodized Diffractive Optic Posterior Chamber Intraocular Lenses, Models MA60d3 and SA60D3", dated Mar. 21, 2005, 29 pgs.
International Search Report and Written Opinion for related application No. PCT/US2011/056279, dated Feb. 1, 2012, 9 pgs.
U.S. Appl. No. 13/427,319, filed Mar. 22, 2012, Grey et al.
U.S. Appl. No. 13/435,103, filed Mar. 30, 2012, Curatu et al.
U.S. Appl. No. 13/681,004, filed Nov. 19, 2012, Frey et al.
Author unknown, "Statement of the Use of Animals in Opthalmic and Visual Research", The Association for Research in Vision and Opthalmology, Obtained from the Internet at: http//www.arvo.org/aboutavro as of Nov. 18, 2010, 3 pgs.
Akchurin, Garif et al., "Evaluation of the degree of turbidity if cataract lens and its correlation with retinal visual acuity", *SPIE*, vol. 3591, Jan. 1999, pp. 74-81.
Al-Ghoul, K. J. et al., "Distribution and Type of Morphological Damage in Human Nuclear Age-Related Cataracts", *Department of Cell Biology and Anatomy, University of North Carolina and Duke University Eye Center*, 1996, pp. 237-251.
Al-Ghoul, Kristin J. et al., "Structural Evidence of Human Nuclear Fiber Compaction as a Function of Ageing and Cataractogenesis", *Exp. Eye Res.*, vol. 72, 2001, pp. 199-214.
Alio, et al., "Crystalline Lens Optical Dysfunction through Aging", *Ophthalmology*, vol. 112, No. 11, Nov. 2005, pp. 2022-2029.
Amann, Josef et al., "Increased Endothelial Cell Density in the Paracentral and Peripheral Regions of the Human Cornea", *American Journal of Ophthalmology*, vol. 135, No. 5, May 2003, pp. 584-590.
Amendt, M. Strauss et al., "Modeling of bubble dynamics in relation to medical applications", *Proc. of SPIE*, vol. 2975, 1997, pp. 362-373.
Ansari, Rafat R. et al., "Measuring lens opacity: combining quasi-elastic light scattering with Scheimpflug imaging system", *Proc. of SPIE*, vol. 3246, 1998, pp. 35-42.
Anschutz, Till, M.D., "Laser Correction of Hyperopia and Presbyopia", vol. 34, No. 4, 1994, pp. 107-137.
Apple, David J. et al., "Preparation and Study of Human Eyes Obtained Postmortem with the Miyake Posterior Photographic Technique", *Ophthalmology*, vol. 97, No. 6, Jun. 1990, pp. 810-816.
Armstrong, Larry "A cataract Breakthrough May Be on the Way", *Business Week*, Mar. 23, 1998, pp. 90-92.
Aston, Adam, "Why Settle for 20/20?", *Business Week*, Mar. 17, 2003, pp. 95-96.
Azzam, Naiel et al., "Long-term lens organ culture system to determine age-related effects of UV irradiation on the eye lens", *Experimental Eye Research*, vol. 79, 2004, pp. 903-911.
Back, Arthur P. et al., "Correction of Presbyopia with Contact Lenses: Comparative Success Rates with Three Systems", *Optometry & Vision Science*, 1989, vol. 66, No. 8, pp. 518-525.
Balaram, Mini et al., Noncontact Specular Microscopy of Human Lens Epithelium, *IOVS*, vol. 41, No. 2, Feb. 2000, pp. 474-481.
Barak, Adiel et al., "Anterior capsulotomy using the $CO_2$ laser", *Proc. of SPIE*, vol. 3246, 1998, pp. 196-198.

(56) References Cited

OTHER PUBLICATIONS

Bath, Patricia E. et al., "Endocapsular Excimer Laser Phakoablation Through a 1-mm Incision", *Opthalmic Laser Therapy*, vol. 2, No. 4, 1987, pp. 245-249.
Beers, A. P. A. et al. "Age-Related Changes in the Accommodation Mechanism", *Optometry and Vision Science*, 1996, vol. 73, No. 4, pp. 235-242.
Beers, A. P. A. et al., "In Vivo Determination of the Biomechanical Properties of the Component Elements of the Accommodation Mechanism", *Vision Res.*, vol. 34, 1994, pp. 2897-2905.
Bellows, John G., M.D. et al., "B. Cataracta Complicata", *Traumatic Cataract*, undated but prior to Jul. 2009, pp. 270-272.
Ben-Sira, I. et al., "Clinical method for measurement of light back scattering from the in vivo human lens", *Invest. Ophthalmol. Vis. Sci.*, vol. 19, No. 4 (Reports), Apr. 1980, pp. 435-437.
Benjamin, William J., "Borish's Clinical Refraction", W.B. Saunders, publishers, copyright 1998, p. 110.
Bettelheim, Frederick A. et al., "Syneretic Response of Aging Normal Human Lens to Pressure", *Investigative Ophthalmology & Visual Science*, vol. 44, No. 1, Jan. 2003, pp. 258-263.
Bigler, Emmanuel, "Depth of field and Scheimpflug's rule: a "minimalist" geometrical approach", published unknown, 2002, pp. 1-17.
Billie, J. F. et al., "3D Imaging of the Human Eye Using the laser Tomographic Scanner Lts", publisher unknown, undated but prior to Jul. 2009, 2 pgs.
Bito, L.Z. et al., "Age-dependent loss of accommodative amplitude in rhesus monkeys: an animal model for presbyopia", *Invest. Ophthalmol. Vis. Sci.*, vol. 23, No. 1, Jul. 1982, pp. 23-31.
Bliss, E. S., "Pulse Duration Dependence of laser Damage Mechamisms", *Opto-Electronics*, vol. 3, 1971, pp. 99-108.
Bor, Zs. PhD., et al., "Plume Emission, Shock Wave and Surface Wave Formation During Excimer Laser Ablation of the Cornea", *Supplement to Retroactive & Corneal Surgery*, vol. 9, Mar./Apr. 1993, pp. S111-S115.
Borja, David et al., "Crystalline Lens MTF Measurement During Simulated Accommodation", *Proc. of SPIE*, 2005, vol. 5688, pp. 26-32.
Borkman, Raymond F. et al., "Evidence for a Free Radical Mechanism in Aging and u.v.—Irradiated Ocular Lenses", *Exp. Eye Res.*, 1977, vol. 25, pp. 303-309.
Braham, Lewis, "Eye Surgery: It's Getting Sharper", *Business Week*, Oct. 18, 2004, pp. 142-143.
Breitenfeld, P. et al., "Finite Element Method-Simulation of the Human Lens During Accommodation", publiasher unknown, vol. 5863, 2005, 9 pgs.
Breitling, Detlef et al., "Fundamental aspects in machining of metals with short and ultrashort laser pulses", *Proc. of SPIE*, vol. 5339, 2004, pp. 1-15.
Brian, G. et al., "Cataract Blindness—Challenges for the 21st Century", *Bulletin of the World Health Organization*, vol. 79, No. 3, 2001, pp. 249-256.
Bron, A.J., "The Ageing Lens", *Opthalmologics*, vol. 214, 2000, pp. 86-104.
Brown, Nicholas, "Dating the onset of cataract", *Transactions of the Ophthalmological Society of the United Kingdom*, vol. 96, 1976, pp. 18-23.
Brown, Nicholas "The Change in Lens Curvature with Age", *Exp. Eye Res.* (1974), vol. 19, pp. 175-183.
Brown, Nicholas "The Change in Shape and Internal Form of the Lens of the Eye on Accommodation", *Exp. Eye Res.* (1973) vol. 15, pp. 441-459.
Burd, H.J. et al., "Can reliable values of Young's modulus be deduced from Fisher's (1971) spinning lens measurements?",*Vision Research*, vol. unknown, 2005, pp. 1-15.
Burd, H.J. et al., "Numerical modeling of the accommodating lens", *Vision Research*, vol. 42, 2002, pp. 2235-2251.
Campbell, Melanie C. W., "Measurement of Refractive Index in an Intact Crystalline Lens", *Vision Research*, vol. 24, No. 5, 1984, pp. 409-415.

Carey, James et al., "Propagation and Characterization of Ultrashort Laser Pulses", Harvard University, 2003, pp. 1-30.
Chaker, M. et al., "Interaction of a 1 psec laser pulse with solid matter", *Phys. Fluids B* 3, vol. 1, Jan. 1991, pp. 167-175, plus cover page.
Charles, M. W. et al., "Dimensions of the Human Eye Relevant to Radiation Protection", *Phys. Med. Biol.*, 1975, vol. 20, No. 2, © 1975, pp. 202-218.
Chen, Wei-Li et al., Ultrasound Biomicroscopic Findings in Rabbit Eyes Undergoing Scleral Suction during Lamellar Refractive Surgery, *IOVS*, vol. 43, No. 12, Dec. 2002, pp. 3665-3672.
Chien, C. Y. et al., "Production of a high-density and high-temperature plasma with an intense high-contrast subpicosecond laser", *Optics Letters*, vol. 18, No. 18, Sep. 15, 1993, pp. 1535-1537.
Claflin, E. S. et al., "Configuring an electrostatic membrane mirror by least-squares fitting with analytically derived influence functions", *J. Opt. Soc. Am. A.*, vol. 3, No. 11, 1986, pp. 1833-1839.
Coleman, D. Jackson et al., "Presbyopia, Accommodation, and the Mature Catenary", *Ophthalmology*, vol. 108, No. 9, Sep. 2001, pp. 1544-1551.
Cook, Christopher A. et al., "Aging of the Human Crystalline Lens and Anterior Segment", *Vision Res.*, 1994, vol. 34, No. 22, pp. 2945-2954.
Corkum, P. B. et al., "Thermal Response of Metals to Ultrashort-Pulse Laser Excitation", *Physical Review Letters*, vol. 61, No. 25, Dec. 19, 1988, pp. 2886-2889.
Costagliola, Ciro et al., "ArF 193 nm Excimer Laser Corneal Surgery as a Possible Risk Factor in Cataractogenesis", *Exp. Eye Res.*, 1994, vol. 58, pp. 453-457.
Cotlier, Edward, M.D., "The Lens", *Adler's Physiology of the Eye*, copyright 2003, pp. 268-290.
Crawford, Kathryn S. et al., "The Role of the Iris in Accommodation of Rhesus Monkeys", *Investigative Ophthalmology & Visual Science*, vol. 31, No. 10, Oct. 1990, pp. 2185-2190.
Croft, Mary Ann et al., "Accommodation and Presbyopia", publisher unknown, vol. 41, 2001, pp. 33-46.
Croft, Mary Ann et al., "Accommodation and Presbyopia: The Ciliary Neuromuscular View", *Opthalmol Clin N Am*, vol. 19, 2006, pp. 13-24.
Croft, Mary Ann et al., Accommodative Ciliary Body and Lens Function in Rhesus Monkeys, I: Normal Lens, Zonule and Ciliary Process Configuration in the Iridectomized Eye, IOVS, vol. 47, No. 3, Mar. 2006, pp. 1076-1086.
Croft, Mary Ann et al., "The Zonula, Lens, and Circumlental Space in the Normal Iridectomized Rhesus Monkey Eye", IOVS, vol. 47, No. 3, Mar. 2006, pp. 1087-1095.
Cromie, William J., "Laser Makes History's Fastest Holes", *The Harvard University Gazette*, 1999, obtained at: http://www.news.harvard.edu/gazette/1999/10.07/laser.html, 6 pags.
Czygan, G. et al., "Mechanical testing of isolated senile human eye lens nuclei", *Med. Eng. Phys.*, vol. 18, No. 5, 1996, pp. 345-349.
Datta, Debajyoti, "Tissue Surgery and Subcellular Photodisruption with Femtosecond Laser Pulses", *Thesis for Dept. of Physics*, Harvard University, May 2002, pp. 1-74.
Dausinger, Friedrich et al., "Micro-machining with ultrashort laser pulses: From basic understanding to technical applications", publisher unknown, undated but prior to Jul. 2009, pp. 1-10.
Dholakia, Sheena A. et al., "Prospective evaluation of phacoemulsification in adults younger than 50 years", *J Cataract Refract Surg*, vol. 31, 2005, pp. 1327-1333.
Douven, Lucien F.A. et al., "Characterization of Mechanical Behaviour of Human Skin In Vivo", *Proc. of SPIE*, vol. 3914, 2000, pp. 618-629.
Du, D. et al.,"Laser-induced breakdown by impact ionization in $SiO_2$ with pulse widths from 7 ns to 150 fs", *Appl. Phys. Lett.*, vol. 64, No. 23, Jun. 6, 1994, pp. 3071-3073.
Ehrmann, Klaus et al., "Evaluation of porcine crystalline lenses in comparison with molded polymer gel lenses with an improved ex vivo accommodation simulator", *Proc. of SPIE*, vol. 5688, 2005, pp. 240-251.
Ehrmann, Klaus et al., "Ex Vivo Accommodation Simulator II—Concept and Preliminary Results", *Proc. of SPIE*, vol. 5314, 2004, pp. 48-58.

(56) References Cited

OTHER PUBLICATIONS

Eisner, Georg, "Eye Surgery—An Introduction to operative technique", Springer-Verlag, Berlin, 1980, pp. 14-19.
El-Osta, Austen a.R. et al., "In vitro model for the study of human posterior capsule opacification", *J Cataract Refract Surg*, vol. 29, 2003, pp. 1593-1600.
Erpelding, Todd N. et al., "Bubble-Based Acoustic Radiation Force for Monitoring Intraocular Lens Elasticity", *IEEE Intl Ultrasonics Symposium*, volue unknown, 2004, pp. 732-735.
Fagerholm, Per P.P., "The Response of the Lens to Trauma", *Trans. Ophtal. Soc. U. K.*, 1982, vol. 102, p. 369-374.
Farnsworth, P.N. et al., "Anterior Zonular Shifts with Age", *Exp. Eye Res.*, vol. 28, 1979, pp. 291-297.
Findl, Oliver et al., "Laserinterferometric Assessment of Pilocarpine-Induced Movement of an Accommodating Intraocular Lens—A Randomized Trial", *Ophthalmology*, vol. 111, No. 8, Aug. 2004, pp. 1515-1521.
Fisher, R.F. et al., "Changes in lens fibres after damage to the lens capsule", publisher unknown, undated but prior to Jul. 2009, 4 pgs.
Fisher, R.F., "Elastic Constants of the Human Lens Capsule", *J. Physiol.*, vol. 201, 1969, pp. 1-19.
Fisher, R.F., "Presbyopia and the Changes With Age in the Human Crystalline Lens", *J. Physiol.*, vol. 228, 1973, pp. 765-779.
Fisher, R. F., "The Ciliary Body in Accommodation", *Trans. Opthalmol. Soc. U.K.*, vol. 105, 1986, pp. 208-219.
Fisher, R.F., "The Elastic Constants of the Human Lens", *J. Physiol.*, vol. 212, 1971, pp. 147-180.
Fisher, R. F. et al., "The elastic constants and ultrastructural organization of a basement membrane (lens capsule)", *Proc. R. Soc. Lond. B.*, vol. 193, 1976, pp. 335-358.
Fisher, R.F., "The Force of Contraction of the Human Ciliary Muscle During Accommodation", *J. Physiol.*, vol. 270, 1977, pp. 51-74.
Fisher, R. F., "The Mechanics of Accommodation in Relation to Presbyopia", *Eye*, vol. 2, 1988, pp. 646-649.
Fleck, Brian W. et al., "Q-switched Nd:YAG laser disruption of rabbit lens nucleus", *Laser and Light in Ophthalmology*, 1990, vol. 3. No. 3, pp. 227-232.
Foster, C. Stephen et al., "Smolin and Thoft's the Cornea: Scientific Foundations and Clinical Practice", *The New England Journal of Medicine*, vol. 353 No. 23, 2005, pp. 2519-2520.
Fujimoto, James et al., "Biomedical Optics", Photonics West, *Proc. of SPIE*, vol. unknown, 2005, pp. 23-70.
Garner, LF et al., "Changes in Equivalent and Gradient Refractive Index of the Crystalline Lens with Accommodation", *Optom, Vis. Sci.*, vol. 74, No. 2, Feb. 1997, pp. 114-119.
Garner, LF et al., "Changes in Ocular Dimensions and Refraction with Accommodation", *Ophthal. Physiol. Opt.*, vol. 17, No. 1, 1997, pp. 12-17.
Garner, Margaret H. et al., "Selective oxidation of cysteine and methionine in normal and senile cataractous lenses", *Proc. Natl. Acad. Sci. USA*, vol. 77, No. 3, Mar. 1980, pp. 1274-1277.
Gayen, Tapan K. et al., "Near-infrared laser welding of aortic and skin tissues and microscopic investigation of welding efficacy", *Proc. of SPIE*, vol. 4949, 2003, pp. 182-185.
Gershenzon, A. et al., "Clinical and Epidemiology—New software for lens retro-illumination digital image analysis", *Australian and New Zealand Journal of Ophthalmology*, 1999, vol. 27, pp. 170-172.
Giblin, Frank J. et al., "Nuclear Light Scattering, Disulfide Formation and Membrane Damage in Lenses of Older Guinea Pigs Treated with Hyperbaric Oxygen", *Exp. Eye Res.*, 1995, vol. 60, pp. 219-235.
Gills, James P., "Treating astigmatism at the time of cataract surgery", *Current Opinion in Ophthalmology*, 2002, vol. 13, pp. 2-6.
Gimbel, Howard V. et al., "Intrastromal Photorefractive Keratectomy with the Nd:YLF Laser", publisher unknown, vol. 34, Iss. 4, 1994, pp. 139-145.
Glasser, Adrian et al., "Accommodative Changes in Lens Diameter in Rhesus Monkeys", *IOVS*s, vol. 47, No. 1, Jan. 2006, pp. 278-286.
Glasser, A. et al., "Biometric, optical and physical changes in the isolated human crystalline lens with age in relation to presbyopia", *Vision Research*, vol. 39, 1999, pp. 1991-2015.
Glasser, Adrian et al., "On modeling the causes of presbyopia", *Vision Research*, vol. 41, 2001, pp. 3083-3087.
Glasser, A. et al., "On the potential causes of presbyopia", *Vision Research*, vol. 39, 1999, pp. 1267-1272.
Glasser, Adrian et al., "Presbyopia and the Optical Changes in the Human Crystalline Lens with Age", *Vision Res.*, vol. 38, No. 2, 1998, pp. 209-229.
Glasser, Adrian et al., "Ultrasound Biomicroscopy of the Aging Rhesus Monkey Ciliary Region", *Optometry and Vision Science*, vol. 78, No. 6, 2001, pp. 417-424.
Goodenough, Daniel A., "Lens gap junctions: a structural hypothesis for nonregulated low-resistance intercellular pathways", *Invest. Ophthalmol. Visual Sci.*, vol. 18, No. 11, Nov. 1979, pp. 1104-1122.
Grace, Jeffery M. et al., "Repetitively Pulsed Ruby Lasers As Light Sources for High-Speed Photography", *Optical Engineering*, vol. 37, No. 8, Aug. 1998, pp. 1-26.
Gwon, Arlene et al., "Focal laser photophacoablation of normal and cataractous lenses in rabbits: Preliminary report", *J Cataract Refract Surg*, vol. 21, May 1995, pp. 282-286.
Habib, Maged S. et al., "Myopic Intrastromal Photorefractive Keratectomy With the Neodymium-Yttrium Lithium Fluoride Picosecond Laser in the Cat Cornea", *Arch Ophthalmol.*, vol. 113, Apr. 1995, pp. 499-505.
Hahn, D.W., "Dynamics of Ablation Plume Particles Generated During Excimer Laser Corneal Ablation", *Lasers in Surgery and Medicine*, vol. 16, 1995, pp. 384-389.
Hamaoui, Marie et al., "Ex-vivo testing of crystalline lens substitutes: a pilot study", *Proc. of SPIE*, vol. 3908, 2000, pp. 123-130.
Hammer, Daniel X. et al., "Dual OCT/SLO Imager with Three-Dimensional Tracker", *Proc. of SPIE*, vol. 5688, 2005, pp. 33-44.
Hammer, Daniel et al., "Shielding Properties of Laser-Induced Breakdown in Water for Pulse Durations From 5 ns to 125 fs", *Applied Optics*, 1997, vol. 36, No. 22, pp. 5630-5640.
Hanson, S.R.A. et al., "The major in vivo modifications of the human water-insoluble lens crystallins are disulfide bonds, deamidation, methionine oxidation and backbone cleavage", *Exp. Eye Res.*, vol. 71, 2000, pp. 195-207.
Hara, Tsutomu, M.D. et al., "Complications associated with endocapsular balloon implantation rabbit eyes", *J Cataract Refract Surg*, vol. 20, Sep. 1994, pp. 507 and 512.
Harding, J. J., "Disulphide Cross-linked Protein of High Molecular Weight in Human Cataractous Lens", *Exp. Eye Res.* (1973), vol. 17, pp. 377-383.
Hartwick, Andrew T. E. et al., "Ephitelial activity of hexokinase and glucose-6-phosphate dehydrogenase in cultured bovine lenses recovering from pharmaceutical-induced optical damage", *Molecular Vision*, vol. 9, 2003, pp. 594-600.
Heisterkamp, Alexander et al., "Nonlinear effects inside corneal tissue after fs-photodisruption", *Proc. of SPIE*, vol. 4433, 2001, pp. 55-60.
Heisterkamp, Alexander et al., "Pulse energy dependence of subcellular dissection by femtosecond laser pulses", *Optics Express*, vol. 13, No. 10, May 2005, pp. 3690-3696.
Hemenger, Richard P. et al., "Change With Age of the Refractive Index Gradient of the Human Ocular Lens", *Investigative Ophthalmology & Visual Science*, Mar. 1995. vol. 36, No. 3. pp. 703-707.
Heys, Karl Robert et al., "Massive increase in the stiffness of the human lens nucleus with age: the basis for presbyopia?", *Molecular Vision*, vol. 10, 2004, pp. 956-963.
Ho, A. et al., "Feasibility of simultaneous correction of ametropia by varying gel refractive index with phaco-ersatz", *Proc. of SPIE*, vol. 4245, 2001, pp. 119-128.
Hoffman, Richard S. et al., "Refractive lens exchange as a refractive surgery modality", Copyright© 2004 Lippincott Williams & Wilkins, pp. 22-28.
Holzer, Mike P. et al., "Corneal flap complications in refractive surgery—Part 1: Development of an experimental animal model", *J Cataract Refract Surg*, vol. 29, Apr. 2003, pp. 795-802.
Holzer, Mike P. et al., "Corneal flap complications in refractive surgery—Part 2: Postoperative treatments of diffuse lamellar keratitis in an experimental animal model", *J Cataract Refract Surg*, vol. 29, Apr. 2003, pp. 803-807.

(56) References Cited

OTHER PUBLICATIONS

Horwitz, Joseph, "α-Crystallin can function as a molecular chaperone", *Proc. Natl. Acad. Sci. USA*, vol. 89. Nov. 1992, pp. 10449-10453.
Hu, Tian-Sheng et al., "Reversal of Galactose Cataract with Sorbinil in Rats", *Investigative Ophthalmology & Visual Science*, May 1983, vol. 24, pp. 640-644.
Huber, G. et al., "Room-temperature 2-μm HO:YAG and 3-μm ER:YAG Lasers", *Journal de Physique*, undated but prior to Jul. 2009, 3 pgs.
Hunter, David, "First, Gather the Data", *New England Journal of Medicine*, vol. 354, No. 4, Jan. 26, 2006, pp. 329-331.
Jacques, Paul F. et al., "Long-term vitamin C supplement use and prevalence of early age-related lens opacities", *Am J Clin Nutr*, 1997; 66, pp. 911-6.
Johannesson, Mattias, "Active Range Imaging 2", PhD-Thesis: SIMD architectures for Range and Radar Imaging, *Linkoping Studies in Science and Technology*, Dissertations No. 399, 2005, pp. 1-34.
Jones, C.E. et al., "Refractive index distribution and optical properties of the isolated human lens measured using magnetic resonance imaging (MRI)", *Vision Research*, vol. 45, 2005, pp. 2352-2366.
Juhasz, Tibor, Ph.D. et al., "Dynamics of Shock Waves and Cavitation Bubbles Generated by Picosecond Laser Pulses in Corneal Tissue and Water", *Lasers in Surgery and Medicine*, vol. 15, 1994, pp. 91-98.
Juhasz, T. et al., "Time resolved observations of shock waves and cavitatin bubbles generated by femtosecond laser pulses in corneal tissue and water", *Lasers in Surgery and Med*, vol. 19, 1996, pp. 23-31.
Juhasz, T. et al., "Time-resolved Studies of Plasma-Mediated Surface Ablation of Soft Biological Tissue with Near-Infrared Picosecond Laser Pulses", *SPIE*, vol. 2975, 1997, pp. 271-281.
Kasthurirangan, Sanjeev et al., "Amplitude dependent accommodative dynamics in humans", *Vision Research*, vol. 43, 2003, pp. 2945-2956.
Kasthurirangan, Sanjeev, "Influence of Amplitude and Starting Point on Accommodative Dynamics in Humans", *IOVS*, vol. 46, No. 9, Sep. 2005, pp. 3463-3472.
Kaufman, Paul L., M.D., "Accommodation and Presbyopia: Neuromuscular and Biophysical Aspects", *Adler's Physiology of the Eye*, date unknown but prior to Jul. 2009, pp. 391-411.
Klem, D. E. et al., "The Interaction of Intense Femtosecond Laser Pulses with Solid Targets", paper prepared under the auspices of the U.S. Dept. of Energy for the Short Wavelength V: Physics with Intense Laser Pulses Second Topical Meeting on Mar. 29-31, published Dec. 30, 1992, 1993, 6 pgs.
Keeney, Arthur H., M.D., "Intralenticular Foreign Bodies", *Arch Ophthal.*, vol. 86, Nov. 1971, pp. 499-501.
König, Karsten et al., "Are Femtosecond Lasers Safe for Ophthalmic Applications?", *Fraunhofer Institute of Biomedical Technologies*, undated but prior to Jul. 2009, pp. 1-16.
König, Karsten et al., "Cornea surgery with nanojoule femtosecond laser pulses", *Proc. of SPIE*, vol. 5688, 2005, pp. 288-293.
König, Karsten et al., "First in vivo animal studies on intraocular nanosurgery and multiphoton tomography with low-energy 80 MHz near infrared femtosecond laser pulses", *Proc. of SPIE*, vol. 5314, 2004, pp. 262-269.
Koopmans, Steven A. et al., "Polymer Refilling of Presbyopic Human Lenses in Vitro Restores the Ability to Undergo Accommodative Changes", *IOVS*, vol. 44, No. 1, Jan. 2003, pp. 250-257.
Koretz, Jane F. et al., "A Model for Accommodation in the Young Human Eye: The Effects of Lens Elastic Anisotropy on the Mechanism", *Vision Res.*, vol. 23, No. 12, 1983, pp. 1679-1686.
Koretz, Jane F. et al., "Accommodation and Presbyopia in the Human Eye—Aging of the Anterior Segment", *Vision Res.*, vol. 29, No. 12, 1989, pp. 1685-1692.
Koretz, Jane F. et al., "Accommodation and Presbyopia in the Human Eye—Changes in the Anterior Segment and Crystalline Lens With Focus", *IOVS*, vol. 38, No. 3, Mar. 1997, pp. 569-578.
Koretz, Jane F. et al., "Analysis of Human Crystalline Lens Curvature as a Function of Accommodative State and Age", *Vision Res.*, vol. 24, No. 10, 1984, pp. 1141-1151.
Koretz, Jane F. et al., "How the Human Eye Focuses", *Scientific American*, Jul. 1988, pp. 92-99.
Koretz, Jane F. et al., "Model of the Accommodative Mechanism in the Human Eye", *Vis. Res.*, vol. 22, 1982, pp. 917-927.
Koretz, Jane F. et al., "Scheimpflug and high-resolution magnetic resonance imaging of the anterior segment: a comparative study", *J. Opt. Soc. Am. A*, vol. 21, No. 3, Mar. 2004, pp. 346-354.
Koretz, Jane F. et al., "The Zones of Discontinuity in the Human Lens: Development and Distribution with Age", *Vision Res.*, vol. 34, No. 22, 1994, pp. 2955-2962.
Krag, Susanne et al., "Biomechanical Characteristics of the Human Anterior Lens Capsule in Relation to Age", *Investigative Ophthalmology & Visual Science*, vol. 38, No. 2, Feb. 1997, pp. 357-362.
Krag, Susanne, "Biomechanical measurements of the lens capsule", *Scandinavian University Theses*, 1999, 3 pgs.
Krag, Susanne et al., "Mechanical Properties of the Human Posterior Lens Capsule", *IOVS*, vol. 44, No. 2, 2003, pp. 691-696.
Krauss, Joel et al., "Laser Interactions With the Cornea", *Survey of Ophthalmology* A689, vol. 31, No. 1, Jul./Aug. 1986, pp. 37-53.
Kronemyer, Bob, "Accommodating IOL? Impossible, Recent Study Seems to Say". *Ocular Surgery News*, http://www.slackmc.com, Sep. 15, 1996, 2 pgs.
Krueger, Ronald R. et al., "Experimental Increase in Accommodative Potential after Neodymium: Yttrium-Aluminum-Garnet Laser Photodisruption of Paired Cadaver Lenses", *Ophthalmology*, vol. 108, No. 11, 2001, pp. 2122-2129.
Krueger, Ronald R. et al., "First safety study of femtosecond laser photodisruption in animal lenses: Tissue morphology and cataractogenesis", *J Cataract Refract Surg*, vol. 31, Dec. 2005, pp. 2386-2394.
Krueger, Ronald R., M.D., et al., "Nonmechanical Microkeratomes Using Laser and Water Jet Technology", Publisher unknown, date unknown but prior to Jul. 2009, pp. 1-33.
Krueger, R.R., "Surf's Up—Catch a wave with a waterjet", *Jrn. Ref. Surg.*, vol. 14, No. 3, May/Jun. 1998, pp. 280-281.
Krueger, Ronald R., M.D. et al., "Ultrastructure of Picosecond Laser Intrastromal Photodisruption", *Journal of Retractive Surgery*, vol. 12, Jul./Aug. 1996, pp. 607-612.
Kuizenga, Dirk J., "FM-Laser Operation of the Nd:YAG Laser", *IEEE Journal of Quantum Electronics*, vol. 6, No. 11, 1970, pp. 673-677.
Kurapkienė, S. et al., "The relationship of ultrasonic and mechanical properties of human nuclear cataract. A pilot study", *Ultragarsas*, vol. 54, No. 1, 2005, pp. 39-43.
Kurtz, Ron et al., "Femtosecond Laser Corneal Refractive Surgery", *Proc. of SPIE*, vol. 3591, 1999, pp. 209-219.
Kurtz, Ron et al., "Ophthalmic Applications of Femtosecond Lasers", *Proc. f SPIE*, vol. 3616, 1999, pp. 51-65.
Kurtz, Ron M. et al., "Optimal Laser Parameters for Intrastromal Corneal Surgery", *Proc. of SPIE*, vol. 3255, 1998, pp. 56-66.
Kurtz, Ron M., MD, et al., "Photo-disruption in the Human Cornea as a Function of Laser Pulse Width", *Journal of Refractive Surgery*, vol. 13, Nov./Dec. 1997, pp. 653-658.
Kuszak, J. R. et al., "A Quantitative Analysis of Sutural Contributions to Variability in Back Vertex Distance and Transmittance in Rabbit Lenses as a Function of Development, Growth, and Age", *Optometry and Vision Science*, vol. 79, No. 3, Mar. 2002, pp. 193-204.
Kuszak, J. R. et al., "Anatomy of Aged and Senile Cataractous Lenses", from "Biochemistry of the Crystalline Lens", undated but prior to Jul. 2009, pp. 564-575.
Kuszak, J. R. et al., "Biochemistry of the Crystalline Lens; Anatomy of Aged and Senile Cataractous Lenses", pp. 564-575.
Kuszak, J. R. et al., "Development of lens sutures", *Int. J. Dev. Biol.*, vol. 48, 2004, pp. 889-902.
Kuszak, J. R. et al., "Electron Microscope Observations of the Crystalline Lens", *Microscopy Research and Technique*, 1996, vol. 33, pp. 441-479.
Kuszak, J. R. et al., "Fibre cell organization in crystalline lenses", *Experimental Eye Research*, vol. 78, 2004, pp. 673-687.

(56) References Cited

OTHER PUBLICATIONS

Kuszak, J. et al., "Gap Junctions of Chick Lens Fiber Cells", *Exp. Eye Res.*, vol. 27, 1978, pp. 495-498.
Kuszak, J. R. et al., "Lens Optical Quality and Lens Sutures", *Investigative Ophthalmology & Visual Science*, vol. 32, No. 7, Jun. 1991, pp. 2123-2129.
Kuszak, J. R. et al., "Lens Optical Quality is a Direct Function of Lens Sutural Architecture", *Investigative Ophthalmology & Visual Science*, vol. 32, No. 7, Jun. 1991, pp. 2119-2129.
Kuszak, J. R. et al., "Quantitative Analysis of Animal Model Lens Anatomy: Accommodative Range is Related to Fiber Structure and Organization", undated but prior to Jul. 2009, 26 pgs.
Kuszak, J. R. et al., "Suppression of Post-Vitrectomy Lens Changes in the Rabbit by Novel Benzopyranyl Esters and Amides", *Exp. Eye Res.*, vol. 75, 2002, pp. 459-473.
Kuszak, JR et al., "The interrelationship of lens anatomy and optical quality II Primate Lenses", *Exp. Eye Res.*, vol. 59, 1994, pp. 521-535.
Kuszak, J. R. et al., "The Relationship Between Rabbit Lens Optical Quality and Sutural Anatomy after Vitrectomy", *Exp. Eye Res.*, vol. 71, 2000, pp. 267-281.
Kuszak Jer R. et al., "The Structure of the Vertebrate Lens", Chapter 4, undated but prior to Jul. 2009, pp. 71-118.
Kuszak, J. et al., "The Surface Morphology of Embryonic and Adult Chick Lens-Fiber Cells", *The American Journal of Anatomy*, vol. 159, 1982, pp. 395-410.
Kuszak, J. R. et al., "The Use of an Ex Vivo Mechanical Stretching Apparatus to Examine Fiber Ultrastructure During Accommodation", undated but prior to Jul. 2009, 1 pg.
Kuwabara, Toichiro, et al., "Electron Microscopic Study of Galactose-Induced Cataract", *Investigative Ophthalmology*, vol. 8, No. 2, Apr. 1969, pp. 133-149.
L'Esperance, Jr. "Ophthalmic Lasers Photocoagulation, Photoradiation and Surgery", $2^{nd}$ Edition, The C.V. Mosby Company, copyright 1983, pp. 529-538.
Lerman, Sidney, et al., "A Method for Detecting 8-Methoxypsoralen in the Ocular Lens", *Science*, vol. 197, Sep. 23, 1977, 1287-1288.
Lerman, Sidney, et al., "Photosensitization of the lens by 8-methoxypsoralen", *Invent. Ophthalmol. Visual Sci.*, vol. 16, No. 11, Nov. 1977, pp. 1065-1068.
Lerman, Sidney, M.D., "Photosensitizing Drugs and Their Possible Role in Enhancing Ocular Toxicity", *Ophthalmology*, vol. 93, No. 3, Mar. 1986, pp. 304-318.
Lerman, Sidney, et al., "Psoralen-long-wave Ultraviolet Therapy and Human Cataractogenesis", *Invent. Ophthalmol. Visual Sci.*, vol. 23, No. 6, Dec. 1982, pp. 801-804.
Lerman, Sidney, et al., "Spectroscopic Evaluation and Classification of the Normal, Aging, and Cataractous Lens", *Ophthl. Res.*, vol. 8, 1976, pp. 335-353.
Lim, Seung Jeong, M.D. et al., "Analysis of zonular-free zone and lens size in relation to axial length of eye with age", *J Cataract Refract Surg*, vol. 24, Mar. 1998, pp. 390-396.
Liu, X. et al., "Competition between Ponderomotive abd Thermal Forces in Short-Scale-Length Laser Plasmas", *Physical Review Letters*, vol. 69, No. 13, Sep. 28, 1992, pp. 1935-1938.
Liu, Xinbing et al., "In vivo plasma-mediated ablation as a function of laser pulse width", *SPIE*, vol. 2975, 1997, pp. 282-288.
Loerscher, Hanspeter et al., "Noncontact Trephination of the Cornea Using a Pulsed Hydrogen Floride Laser", *American Journal of Ophthalmology*, vol. 104, Nov. 1987, pp. 471-475.
Loesel, Frieder H. et al., "Laser-Induced Optical Breakdown on Hard and Soft Tissues and Its Dependence on the Pulse Duration: Experiment and Model", *IEEE Journal of Quantum Electronics*, vol. 32, No. 10, Oct. 1996, pp. 1717-1722.
Lou, Marjorie F., et al., "Protein-Thiol Mixed Disulfides in Human Lens", published by Academic Press Limited, 1992, pp. 889-896.
Lubatschowski, Holger, "Surgical Laser System for the Treatment of Presbyopia", $7^{th}$ *Biotech in Europe Investor Forum*, Switzerland, Oct. 2-3, 2007, 9 pgs.
Lutze, Margaret et al., "Lenses of Diabetic Patients "Yellow" at an Accelerated Rate Similar to Older Normals", *Investigative Ophthalmology & Visual Science*, vol. 32, No. 1, Jan. 1991, pp. 194-199.
Maguen, Ezra, et al., "Excimer Laser Ablation of the Human Lens at 308 nm with a Fiber Delivery System", *J. Cataract Refract Surg.*, vol. 15, Jul. 1989, pp. 409-414.
Manns, Fabrice et al., "Radius of Curvature and Aspericity of the Anterior and Posterior Surface of Human Cadaver Crystalline Lenses", *Experimental Eye Research*, 2004, vol. 78, pp. 39-51.
Marion, II, John E. et al., "Medical Applications of Ultra-Short Pulse Lasers", *Proc. of SPIE*, vol. 3616, 1999, pp. 42-50.
Masters, B.R., "Three-dimensional Microscopic Tomographic Imaging of the Cataract in a Human Lens in Vivo", *Optics Express* 332, vol. 3, No. 9, Oct. 1998, pp. 332-338.
Mathias, R.T. et al., "Physiological Properties of the Normal Lens", *Physiological Reviews*, vol. 77, No. 1, Jan. 1997, pp. 21-50.
McBrien, N. A et al., "Experimental Myopia in a Diurnal Mammal (*Sciurus* Carolinesis) with No Accommodative Ability", *J. Physiol.*, vol. 469, 1993, pp. 427-441.
McCourt, M. E et al., Refractive State, Depth of Focus, and Accommodation of the Eye of the California ground squirrel (Spermophiliu Beecheyi), *Vision Res*, vol. 24, No. 10, 1984, pp. 1261-1266.
McDonald, Marguerita B., et al., "Central Photorefractive Keratectomy for Myopia, The Blind Eye Study", *Arch Ophthalmol*, vol. 108, Jun. 1990, pp. 799-808.
Michael, Ralph et al., "Refractive Index of Lens Fiber Membranes in Different Parts of the Crystalline Lens", *Proceedings of SPIE*, vol. 4611, 2002, pp. 159-164.
Moffat, B.A. et al., "Age-Related Changes in Refractive Index Distribution and Power of the Human Lens as Measured by Magnetic Resonance Micro-Imaging In Vitro", *Vision Research*, vol. 42, 2002, pp. 1683-1693.
Müller, F. et al., "A Comparative Study of Deposition of Thin Films by Laser Induced PVD with Femtosecond and Nanosecond Laser Pulses", *SPIE*, vol. 1858, 1993, pp. 464-474.
Mutti, Donald O., et al., "A Video Technique for Phakometry of the Human Crystalline Lens", *Investigative Ophthalmology, & Visual Science*, vol. 33, No. 5, Apr. 1992, pp. 1771-1781.
Myers, Raymond I. et al., "Feasibility of Using Lasers to Retard Cataract Development in the Ocular Lens by Restoring Lens Movement"; undated but prior to Jul. 2009, pp. 1-22.
Myers, Raymond I. et al., "Novel Approaches to Correction of Presbyopia With Laser Modification of the Crystalline Lens", *Journal of Refractive Surgery*, vol. 14, Mar./Apr. 1998; pp. 136-139.
Nanevicz, Tania M., et al., "Excimer Laser Ablation of the Lens", *Arch Ophthamol*, vol. 104, Dec. 1986, pp. 1825-1829.
Naranjo-Tackman, Ramon et al., "Subepithelial arquate (sic) incisions, using the femtosecond surgical laser, in post-phaco astigmatism: Preliminary visual and refractive results", a powerpoint presentation shown at ESCRS meeting held in London England in Sep. 2006, 8 pgs.
Neev, Joseph, "Ultrashort Pulse Lasers: A New Tool for Biomedical Applications", *SPIE*, vol. 3255; pp. 2-7.
Nichamin, Louis D., "Treating astigmatism at the time of cataract surgery", *Current Opinion in Ophthalmology*, 2003, vol. 14, p. 35-38.
Oberheide, Uwe et al., "Therapy Monitoring of Laser Cyclophotocoagulation", Proceedings of *SPIE*, vol. 4611, 2002, pp. 48-53.
O'Donnell, Colleen B., et al., "Ablation Smoothness as a Function of Excimer Laser Delivery System", *J. Cataract Refract Surg.*, vol. 22, Jul./Aug. 1996, pp. 682-685.
O'Donnell, Colleen B., et al., "Surface Roughness in PMMA is Linearly Related to the Amount of Excimer Laser Ablation", *Journal of Refractive Surgery*, vol. 12, Jan./Feb. 1996, pp. 171-174.
Oriowo, Olanrewaju Matthew, "A Study of Ultraviolet Radiation Effects on Procine Crystalline Lens and Development of a New Assay Methodology for UV Cataractogenesis Investigation", *A Thesis Presented to the University of Waterloo*, 2000, pp. i-xix and 1-218.
Ostrin, Lisa A. et al., "Comparisons Between Pharmacologically and Edinger-Westphal-Stimulated Accommodation in Rhesus Monkeys", *Investigative Ophthalmology & Visual Science*, 2005, vol. 46, No. 2, pp. 609-617.

(56) References Cited

OTHER PUBLICATIONS

Ostrin, Lisa A. et al., "Effects of Pirenzepine on Pupil Size and Accommodation in Rhesus Monkeys", *Investigative Ophthalmology & Visual Science*, Oct. 2004, vol. 45, No. 10, pp. 3620-3628.

Ostrin, Lisa A. et al., "The Effects of Phenylephrine on Pupil Diameter and Accommodation in Rhesus Monkeys"; *Investigative Ophthalmology & Visual Science*, 2004, vol. 45, No. 1, pp. 215-221.

Parel, Jean-Marie et al., "Intraocular Implants for the Surgical Correction of Presbyopia"; *In Ophthalmic Technologies X*, Proceedings of SPIE, vol. 3908, 2000, pp. 115-122.

Patel, C.K. et al., "The Ageing Lens", *Association of Optometrists, City University, London*; undated, www.optometry.co.uk; pp. 27-31.

Pau, Hans et al., "The increasing sclerosis of the human lens with age and its relevance to accommodation and presbyopia", *Graefe's Arch Clin Exp. Ophthalmol.*, (1991) vol. 229, pp. 294-296.

Payne, Peter A. et al., "Ophthalmic Applications of Laser-Generated Ultrasound"; *SPIE*, 2000, vol. 3908, pp. 13-22.

Peterson, Jennifer A. et al., "Intraocular Pressure Measurement in Cynomolgus Monkeys, Tono-Pen Versus Manometry", *Investigative Ophthalmology & Visual Science*, 1996, vol. 37, No. 6, pp. 1197-1199.

Prokofeva, G. I et al., "Effects of Low-Intensity Infrared Laser Irradiation on the Eye, (An Experimental Study)", *Vestn. Oftalmol.*, vol. 112, No. 1, 1996, pp. 31-32, with English Abstract, 5 pgs.

Puliafito, Carmen A., M.D. et al., "High-Speed Photography of Excimer Laser Ablatio of the Cornea", *Arch Ophthalmol*, vol. 105, Sep. 1987, pp. 1255-1259.

Qian, Wen et al., "3 Year Simvastatin Treatment and Lens Nuclear Back Scattering"; *J Ophthalmol*, vol. 84, 2000, pp. 512-516.

Qian, Wen et al., "Universal Opacity Standard for Scheimpflug Photography", *Ophthalmic Res*, 2000, vol. 32, pp. 292-298.

Rafferty, Nancy et al., "Lens Wound Healing and Cataractogenesis in a Pigmented Eye", *Exp. Eye Res.* (1984), vol. 38, pp. 267-277.

Riley, Michael V., et al., "The Effects of UV-B Irradiation on the Corneal Endothelium", *Eye Research Institute of Oakland University*, 1987, pp. 1021-1033.

Ripken, T. et al., "FEM Simulation of the Human Lens Compared to Ex-Vivo Porcine Lens Cutting Pattern: A Possible Treatment of Presbyopia"; undated, 11 pgs.

Ripken T. et al., "First in-vivo studies of Presbyopia treatment with ultrashort laser pulses", *Proc. SPIE 5142*, vol. 137, 2003, 9 pgs.

Ripken, T. et al., "Fs-laser Induced Elasticity Changes to Improve Presbyopic Lens Accommodation", undated, 10 pgs.

Ripken T. et al., "Investigations for the correction of Presbyopia by fs-laser induced cuts", *Proc. SPIE 5314*, vol. 27, 2004, 9 pgs.

Rockwell, B.A. et al., "Safe Use of Ultra-short Lasers"; *SPIE*, vol. 3616, 1999, pp. 32-39.

Roesner, C.A.D. et al., "Light-Matter Interactions on the FEMTOSECOND Time Scale", *Department of Physics and Division of Engineering and Applied Sciences, Harvard University*; undated, pp. 1-27.

Rol, Pascal et al., "An Optomechanical Eye Model for Observation of Lens Photoablation"; *SPIE*, 1997, vol. 2971, pp. 171-174.

Sacks, Zachary S. et al., "Laser Spot Size as a Function of Tissue Depth and Laser Wavelength in Human Sclera", *SPIE*, 1998, vol. 3255, pp. 67-76.

Sauteret, C. et al., "Laser designers eye petawatt power", *Laser Focus World*, Oct. 1990, pp. 85-92 with cover page.

Scammon, Richard J. et al., "Simulations of Shock Waves and Cavitation Bubbles Produced in Water by Picosecond and Nanosecond Laser Pulses", *SPIE*, 1998, vol. 3254, pp. 264-275.

Schachar, Ronald A. MD, PhD., et al., "A Revolutionary Variable Focus Lens", *Annals of Ophthalmology*, vol. 28, No. 1, Jan./Feb. 1996, pp. 11-18.

Schachar, Ronald A., M.D., "Cause and Treatment of Presbyopia With a Method for Increasing the Amplitude of Accommodation", *Annals of Ophthalmol*, 1992, vol. 24, pp. 445-452.

Schachar, Ronald A., M.D. et al., "Experimental Destruction of Cataractous Lenses by Laser", *Ophthalmic Surgery*, Surgical Forum, pp. 506-509.

Schachar, Ronald A., M.D. et al., "Experimental Support for Schachar's Hypothesis of Accommodation", *Ann Ophthalmol*, 1993; vol. 25, pp. 404-409.

Schachar, Ronald A., MD, PhD, "Histology of the Ciliary Muscle-Zonular Connections", *Annals of Ophthalmology*, vol. 28, No. 2, Mar./Apr. 1996, pp. 70-79.

Schachar, Ronald A. MD et al., "Mechanism of Human Accommodation as Analyzed by Nonlinear Finite Element Analysis", *Ann Ophthalmol*; 2001; vol. 33, No. 2, pp. 103-112.

Schachar, Ronald A., MD, PhD, "Pathophysiology of Accommodation and Presbyopia, Understanding the Clinical Implications", *J. Florida M.A.*, vol. 81, No. 4, Apr. 1994, pp. 268-271.

Schaeffel, Frank, "Kappa and Hirschberg Ratio Measured With an Automated Video Gaze Tracker", *Optometry and Vision Science*, 2002, vol. 79, No. 5, pp. 329-334.

Schaffer, Chris B. et al., "Dynamics of Femtosecond Laser-Induced Breakdown in Water From Femtoseconds to Microseconds", *Optics Express*, 2002, vol. 10, No. 3, pp. 196-203.

Schaffer, Chris B. et al., "Morphology of Femtosecond Laser-Induced Structural Changes in Bulk Transparent Materials", *Applied Physics Letters*, vol. 84, No. 9, 2004, pp. 1441-1443.

Shen, Nan, et al., "Ablation of Cytoskeletal Filaments and Mitochondria in Live Cells Using a Femtosecond Laser Nanoscissor", MCB, 2005, vol. 2, No. 1, pp. 17-25.

Shen, Nan; "Photodisruption in Biological Tissues Using Femtosecond Laser Pulses", *A Thesis Presented to the Department of Physics, Harvard University*, 2003, pp. 1-125.

Shen, Nan, et al., "Photodisruption in Biological Tissues and Single Cells Using Femtosecond Laser Pulses", undated, 2 pgs.

Shen, Nan, et al., "Surface and Bulk Photodisruption in Turbid Tissue Using Femtosecond Laser Pulses", *Department of Physics and Division of Engineering and Applied Sciences, Harvard University*, undated, pp. 1-24.

Sher, Neal A., MD, "Hyperopic Refractive Surgery", *Current Opinion in Ophthalmology*, 2001, vol. 12, pp. 304-308.

Sivak, Jacob G., "Through the Lens Clearly: Phylogeny and Development, The Proctor Lecture", *Ophthalmology & Visual Science*, 2004, vol. 45, No. 3, pp. 740-747.

Sliney, D. H et al., "Medical Lasers and Their Safe Use", *Springer Verlag*, New York, 1993, pp. 42-50.

Slingsby, Christine, "Lens Crystallin Crystal Structures", undated article, 3 pgs.

Söderberg, Per G., et al., "Angular Dependence of the Intensity of Back Scattered Light From Human Lenses With Nuclear Cataract, Implications for Measurement", *SPIE*, 2000, vol. 3908, pp. 34-37.

Söderberg, Per G., et al., "External Standard for Measurements with the Scheimpflug Slitlamp Microscope", *SPIE*, 1997, vol. 2971, pp. 8-13.

Soileau, M. J. et al., "Temporal Dependence of laser-Induced Breakdown in NaCl and $SiO_2$", prepared for Dept. of Physics, North Texas State University, publication date unknown, 19 pgs.

Solomon, Ira Seth, M.D., "Aqueous Humor Dynamics", undated, 17 pgs.

Spector, Abraham, "Aging of the Lens and Cataract Formation", *Aging and Human Visual Function*, pp. 27-43.

Srinivasan, R., "Ablation of Polymers and Biological Tissue by Ultraviolet Lasers", Oct. 1986, pp. 932-935.

Srinivasan R. et al., "Excimer Laser Surgery of the Cornea", *American Journal of Ophthalmology*, vol. 96, 1993, pp. 710-715.

Stitzel, Joel D., et al., "A Nonlinear Finite Element Model of the Eye With Experimental Validation for the Prediction of Globe Rupture", *Stapp Car Crash Journal*, 2002, vol. 45, 24 pgs.

Stitzel, Joel D., et al., "Blunt Trauma of the Aging Eye", *Arch Ophthalmol*, 2005, vol. 123, pp. 789-794.

Strauss, Moshe, et al., "Two-Dimensional Rayleigh Model of Vapor Bubble Evolution", *SPIE*, 1999, vol. 3601, pp. 212-224.

Strenk, Susan A., et al, "Age-Related Changes in Human Ciliary Muscle and Lens: A Magnetic Resonance Imaging Study", *Investigative Ophthalmology & Visual Science*, 1999, vol. 40, No. 6, pp. 1162-1169.

Strenk, Susan A. et al., "Magnetic Resonance Imaging Study of the Effects of Age and Accommodation on the Human Lens Cross-Sectional Area", *IOVS*, 2004, Vo. 45, No. 2, pp. 539-545.

(56) References Cited

OTHER PUBLICATIONS

Strenk, Susan A., et al, "The Mechanism of Presbyopia", *Progress in Retinal and Eye Research*, 2004 vol. 11, pp. 1-15.
Stuart, B. C. et al., "Laser-Induced Damage in Dielectrics with Nanosecond to Subpicosecond Pulses", *Physical Review Letters*, vol. 74, No. 12, Mar. 20, 1995, pp. 2248-2251.
Sweeney, Matthew H.J., et al., "Movement of Cysteine in Intact Monkey Lenses: The Major Site of Entry is the Germinative Region", *Experimental Eye Research*, 2003, vol. 77. pp. 245-251.
Swegmark, Gunnar, "Studies With Impedance Cyclography on Human Ocular Accommodation at Different Ages", *ACTA Ophthalmologica*, vol. 47, 1969, pp. 1186-1206.
Taboada, J., et al., "Optically Coupled Technique for Photorefractive Surgery of the Cornea", *Optics Letters*, vol. 15, No. 9, May 1, 1990, pp. 458-460.
Taboada, J. et al., "Response of the Corneal Epithelium to KrF Excimer Laser Pulses", *Health Physics*, vol. 30, 1981, pp. 677-683.
Tahi, Hassan, et al., "Restoring Accommodation: Surgical Technique and Preliminary Evaluation in Rabbits", *SPIE*, 1999, vol. 3591, pp. 267-269.
Tamm, Svenja, et al., "Age-Related Changes of the Human Ciliary Muscle. A Quantitative Morphometric Study", *Mechanisms of Aging and Development*, vol. 62, 1992, pp. 209-221.
Tang, Daxin; "Influence of Age, Diabetes, and Cataract on Calcium, Lipid-Calcium, and Protein-Calcium Relationships in Human Lenses", *Investigative Ophthalmology & Visual Science*, 2003, vol. 44, No. 5, pp. 2059-2066.
Taylor, Virginia L. et al., "Morphology of the Normal Human Lens", *Investigative Ophthalmology & Visual Science*, Jun. 1996, vol. 37, No. 7, pp. 1396-1410.
Topilow, Harvey W., M.D., "Vitreous Changes in Retinal Branch Vein Occlusion", *Arch Ophthalmol*, vol. 105, Sep. 1987, 2 pgs.
Trokel, Stephen L., M.D., et al., "Excimer Laser Surgery of the Cornea", *American Journal of Ophthalmology*, vol. 96, No. 6, Dec. 1983, pp. 710-715.
Tsai, Philbert S., "All-Optical, In-Situ Histology of Neuronal Tissue with Femtosecond Laser Pulses", *Imaging in Neuroscience and Development*, CSHL Press, undated, 12 pgs.
Tsubota, Kazuo, "Application of Erbium:YAG Laser in Ocular Ablation", *Ophthalmologica*, 1990, vol. 200, pp. 117-122.
Van Alphen, G.W.H.M. et al., "Elasticity of Tissues Involved in Accommodation", *Vision Res.*, vol. 31, No. 7/8, 1991, pp. 1417-1438.
Venugopalan, V. et al., "The Thermodynamic Response of Soft Biological Tissues to Ultraviolet Laser Irradiation", *Biophysical Journal*, vol. 60, Oct. 1995, pp. 1258-1271.
Vilupuru, Abhiram S., "Optical and Biometric Relationships of the Isolated Pig Crystalline Lens", *Ophthal. Physiol. Opt.*, 2001, vol. 21, No. 4, pp. 296-311.
Vilupuru, Abhiram S., "Spatially Variant Changes in Lens Power During Ocular Accommodation in a Rhesus Monkey Eye", *Journal of Vision*, 2004, vol. 4, pp. 299-309.
Vogel, Alfred et al., "Factors Determining the Refractive Effects of Intrastromal Photorefractive Keratectomy with the Picosecond Laser", *J. Cataract Refract Surg.*, vol. 23, Nov. 1997, pp. 1301-1310.
Vogel, Alfred et al., "Interaction of Laser-Produced Cavitation Bubbles With an Elastic Tissue Model", *SPIE*, 2001, vol. 4257, pp. 167-177.
Vogel, Alfred et al., "Intraocular Photodisruption With Picosecond and Nanosecond laser Pulses: Tissue Effects in Cornea, Lens and Retina", *Investigative Ophthalmology & Visual Science*, Jun. 1994, No. 7, vol. 35, pp. 3032-3044.
Vogel, Alfred et al., "Kinetics of Phase Transitions in Pulsed IR Laser Ablation of Biological Tissues", *SPIE*, 2003, vol. 4961, pp. 66-74.
Vogel, Alfred et al., "Laser-Induced Breakdown in the Eye At Pulse Durations From 80 ns to 100 fs", *SPIE*, 1998, vol. 3255, pp. 34-49.
Vogel, Alfred et al., "Numerical Simulation of Optical Breakdown for Cellular Surgery at Nanosecond to Femtosecond Time Scales", *SPIE*, 2001, vol. 4433, pp. 70-80.
Vrensen, G. F. J. M., "Aging of the human eye lens—A morphological point of view", *Comp. Biochem. Physiol.*, vol. 111A, 1995. pp. 519-553.
Waring III, George O., M.D., "Presbyopia and Accommodative Intraocular Lenses—the Next Frontier in Refractive Surgery?", *Refractive & Corneal Surgery*, vol. 8, Nov./Dec. 1992, pp. 421-423.
Weale, Robert D., Sc., "Presbyopia Toward the End of the 20th Century", *Survey of Ophthalmology*, vol. 34, No. 1, Jul.-Aug. 1989, pp. 15-29.
Werblin, Theodore P., M.D., "Should We Consider Clear Lens Extraction for Routine Refractive Surgery?", *Refractive & Corneal Surgery*, vol. 8, Nov./Dec. 1992, pp. 480-481.
Werner, Liliana, MD, et al., "Capsular Bag Opacification After Experimental Implantation of a New Accommodating Intraocular Lens in Rabbit Eyes", *J Cataract Refract Surg.*, 2004, vol. 30, pp. 1114-1123.
Werner, Liliana, MD. et al., "Posterior Capsule Opacification in Rabbit Eyes Implanted With 1-Piece and 3-Piece Hydrophobic Acrylic Intraocular Lenses", *J Cataract Refract Surg*, 2005, vol. 31, pp. 805-811.
Wilks, S. C. et al., "Absorption of ultra-Intense Laser Pulses", *Physical Review Letters*, vol. 69, No. 9, Aug. 31, 1992, pp. 1383-1386.
Wyatt, Harry J., "Application of a Simple Mechanical Model of Accommodation to the Aging Eye", *Eye Res.*, vol. 33, No. 5/6, 1993, pp. 731-738.
Ziebarth, Nöel, et al; "Non-contact Optical Measurement of Lens Capsule Thickness During Simulated Accommodation", *SPIE*, 2005, vol. 5688, pp. 19-25.
Zuclich, Joseph A. et al., "A comparison of laser-induced retinal damage from infrared wavelengths to that from visible wavelengths", *Lasers and Light*, vol. 8, No. 1, 1997, pp. 15-29.
Zuclich, Joseph A. et al., "In Situ Measurements of Lens Fluorescence and its Interference With Visual Function", *Investigative Ophthalmology & Visual Science*, vol. 33, No. 2, 1993, pp. 410-415.
Zuclich, Joseph, "In Vivo Measurements of Optical Properties of the Ocular Lens", Reprinted from Proceedings of Ultraviolet Radiation Hazards, Jan. 26-27, 1994, *SPIE-The International Society for Optical Engineering*, Vo. 2134B Ultraviolet Radiation Hazards, 1994, pp. 99-112.
Zuclich, J.A., et al., "Ocular Effects of Penetrating IR Laser Wavelengths", Reprinted from Proceedings of Laser-Tissue Interaction VI, Feb. 6-9, 1995, *SPIE-The International Society for Optical Engineering*, vol. 2391, 1995, pp. 111-125.
Zuclich, Joseph A., et al., "Rapid Noninvasive Optical Characterization of the Human Lens", *Lasers in the Life Sciences*, 6(1), 1994, pp. 39-53.
Zuclich, Joseph A., "Research on the Ocular Effects of Laser Radiation", Published by *Technology Incorporated: Life Sciences Division*, publication date unknown, 59 pgs.
Zuclich, Joseph A., "Ultraviolet-Induced Photochemical Damage in Ocular Tissues", *Health Physics*, vol. 56, No. 5, May 1989, pp. 671-681.
Zuclich, Joseph A., "Workshop on Long-Term Visual Health Risks of Optical Radiation -Thermal Cataracts Induced by Uv Laser Radiation", *Workshop Report, Cataract Working Group*, publisher unknown, publication date unknown, 13 pgs.
Agrahari, S. et al., "The Potential of Photodisruption Laser Treatment of the Crystalline Lens to Rupture the Lens Capsule", *ARVO Abstract* No. 07-A-6800, 2006, 1 pg.
Faraggi, E. et al., "Stress confinement, shock wave formation and laser induced damage", Conference 5695: Optical Interactions with Tissue and Cells XVI, *Photonics West*, undated, 1 pg.
Fisher, R F, "The ciliary body in accommodation", *Trans Ophthalmol. Soc. UK*, 1989, vol. 105,1 pg.
Fisher, RF. "The mechanics of accommodation in relation to presbyopia", *Eye*, 1988, vol. 2, 1 pg.
Frey, R. W. et al., "Modification of Lens Mechanics of Human Cadaver and Porcine Lenses Using Photodisruption Laser to Change Lens Power and Increase Flexibility", *ARVO Abstract* No. 07-A-06652, 2006, 1 pg.
Garner, LF et al., "Changes in equivalent and gradient refractive index of the crystalline lens with accommodation", *Optom Vis. Sci.*, 1997, vol. 74,1 pg.

(56) References Cited

OTHER PUBLICATIONS

Garner LF et al., "Changes in ocular dimensions and refraction with accommodation", *Ophthalmic Physiol. Opt.*, 1997, vol. 17, 1 pg.

Gray, G. et al., "Constructions of a Computer Mesh Model of the Anatomical Human Crystalline Lens Fiber Ultrastructure", *ARVO Abstract*, 2006, 1 pg.

Helsterkamp, A. et al., "Nanosurgery in live cells using ultrashort laser pulses", Conference 5695: Optical Interactions with Tissue and Cells XVI, *Photonics West*, undated, 1 pg.

Kuszak, J.R., "Progressively More Complex Star Sutures Formed in Primate Lenses During Periods of Development, Growth and Aging Are Related to Accommodation", *Abstracts Online*, obtained from the Internet on Apr. 19, 2006 at: http://www.abstractsonline.com/viewer/viewAbstractPrintFriendly.asp?CKey={C8FDF5D . . . Apr. 19, 2006, I page.

Kuszak, J. R. et al., "Results From a Finite Element Model Analysis of the Accommodative Process Based on the Human Crystalline Lens Fiber Ultrastructure", *ARVO Abstract*, 2006, 1 pg.

McBrien Na et al., "Experimental myopia in a diurnal mammal (*Sciurus carolinensis*) with no accommodative ability", *J Physiol.*, 1993, vol. 469, 1 pg.

McCourt Me et al., "Refractive state, depth of focus and accommodation of the eye of the California ground squirrel (*Spermophilus beecheyi*)", *Vision Res.*, 1984, vol. 24, 1 pg.

Oberheide, U. et al., "Flexibility Increase of Human Donor Lenses After Femosecond Laser Treatment (fs-Lentotomy)", *ARVO Abstract* No. 3833/B571, 2007, 2 pgs.

Olmstead, T. et al., "The Use of an Off Axis Slit Laser Camera System for Determining Photodisruptive Laser Placement in Lenses", *ARVO Abstract* No. 07-A-5967, 2006, 1 pg.

Rafferty, NS. et al., "Comparative study of actin filament patterns in lens epithelial cells, Are these determined by the mechanisms of lens accommodation?", *Curr Eye Res.*, 1989, vol. 8, 1 pg.

Roa, Ch. Mohan et al., "Level of Reduced Nucleotides and Lens Photodamage", *National Eye Institute*, undated, 1 pg.

Subramaniam, H. et al., "Finite Element Analysis of the Accommodative Process in the Whole Globe", *ARVO Abstract* No. 07-A-6249, 2006, 1 pg.

Van Alphen Gw et al., "Elasticity of tissues involved in accommodation", *Vision Res.*, 1991, vol. 31,1 pg.

Wang, B. et al., "In-vivo animal studies on intraocular nanosurgery with low-energy 80 MHZ near infrared femtosecond laser pulses", Conference 5695: Optical Interactions with Tissue and Cells XVI, *Photonics West*, undated, 1 pg.

Yeilding, R. H. et al., "Lens Culture System for Long Term Study of Porcine Lenses Pre and Post Laser Photodisruption Treatment", *ARVO Abstract* No. 01-A-6495, 2006, 1 pg.

Zepkin, N. et al., "Measurement of Temperature Rise in Porcine Crystalline Lenses from a Photodisruption Laser", *ARVO Abstract* No. 07-A-6709, 2006, 1 pg.

Zoltoski, R. K. et al., "Reverse Engineering of Human Lenses", *ARVO Abstract* No. 2018/B159, 2007, 2 pgs. Presentation Materials.

AVRO, "Statement for the Use of Animals in Ophthalmic and Visual Research", *The Association for Research in Vision and* Ophthalmology, copyright © 2002, obtained from the Internet on Jan. 15, 2005 at: http://www.avro.org/AboutAvro/animalst.asp, 3 pgs.

Gattass, Rafael et al., "Femtosecond laser micromaching Applications in Technology and Biology", Photonics West conference Jan. 2005, 78 pgs.

Hermans, E. et al., "Estimating the External Force Acting on the Human Eye Lens During Accommodation Using Finite Elements Modeling", presentation on Accommodation & Presbyopia, May 2005, 1 pg.

Kuszak et al., "Light, scanning and electron micrographs have lead to the following interpretations of secondary fiber formation", 2004, 16 pgs.

Lubatschowski, H. et al., "Treatment of Presbyopia by Cutting the Cystaline Lens: A Comparison of FEM Simulation and Ex vivo Studies", *Lazer Zentrum Hannover e.V.*, Publication date unknown, 22 pgs.

Mazur, Eric, "An Introduction to Femtosecond Laser Science", Photonics West conference Jan. 2005, 291 pgs.

Nebel, Achim et al., "Fast Micromachining using Picosecond Lasers", Photonics West conference Jan. 2005, 37 pgs.

OSN SuperSite, "Increase in lens stiffness with age may cause presbyopia, study suggests", 2005, 1 pg.

"Presbyopia —preconditions", *Laser Zentrum Hannover*, undated, 11 pgs.

"Principles of Ultrafast Laser Surgery Femtosecond Laser-Tissue Interaction", copyright © Center for Ultrafast Optical Sciences, Un. Of Michigan, undated, 3 pgs.

Roundy, Carlos—"Propagation factor qualifies leaser bean performance", *Laser World Focus*, undated, 3 pgs.

Shen, J. et al. "Measurement of the Lens Capsule Contraction Force in the Radial Direction", presentation on Accommodation & Presbyopia, May 2005, 1 pg.

Figure 4.2—Optical constants for a "standard eye", publication unknown, undated, 1 pg.

Picture of an eye obtained from the Internet on Mar. 28, 2005 at: http://www.opt.uh.edu/research/aglasser/aao/gonioani.gif, 1 pg.

Pictures of eyes, date and publisher unknown, 5 pgs.

Loesel paper graphs, date and publisher unknown, 2 pgs.

U.S. Appl. No. 14/142,255, date Dec. 27, 2013, Naranjo-Tackman et al.

Unpublished U.S. Appl. No. 14/142,255, filed Dec. 27, 2013, 25 pgs.

\* cited by examiner

SYSTEM AND METHOD OF SCAN CONTROLLED ILLUMINATION OF STRUCTURES WITHIN AN EYE

This application claims the benefit of priority under 35 U.S.C. §119 (e)(1) of U.S. Provisional Application Ser. No. 61/455,178, filed Oct. 15, 2010, the entire contents of which is incorporated herein by reference.

BACKGROUND OF THE INVENTION

1. Field of the Invention

The present inventions relate to methods and systems for illuminating, obtaining images of, and determining the shape and position of structures within an eye, and in particular, the cornea, natural human crystalline lens and adjacent structures of the eye. More particularly, the present inventions relate to variably controlled scanning of laser light illumination of such structures, controlled and predetermined digital capture of the images of the illuminated structures with an accurately calibrated digital camera and the creation of enhanced digital composite images of the illuminated structures.

2. Description of the Related Art

Presbyopia most often presents as a near vision deficiency, the inability to read small print, especially in dim lighting after about 40-45 years of age. Presbyopia, or the loss of accommodative amplitude with age, relates to the eye's inability to change the shape of the natural crystalline lens, which allows a person to change focus between far and near, and occurs in essentially 100% of the population. Accommodative amplitude has been shown to decline with age steadily through the fifth decade of life.

Cataracts, or the condition when the natural crystalline lens becomes opaque and clouds vision, occurs in millions of people per year and are treated effectively with surgical techniques, such as ultrasonic phacoemulsification pioneered by Kelman 30 years ago. Although the techniques have been refined over the years, safety concerns from ocular trauma, especially to the corneal endothelium from the ultrasonic energy required to break up a hardened cataract, is undesirable; especially for those with a compromised corneal endothelium, such as those with Fuchs Dystrophy. Moreover, the use of lasers in the treatment of cataracts has a further issue. Cataracts scatter light, including laser light, and thus, can prevent a laser treatment beam from having the desired tissue effect. Moreover, the light scattering effect of cataracts and other opacifications can make optically determining the position and shape of the lens difficult.

The established treatment for cataracts is the removal of the opacified human crystalline lens and its replacement with an intraocular lens ("IOL"). In general, IOLs include a small plastic lens with plastic side struts, called haptics, to hold the lens in place within the capsular bag inside the eye. Exemplary types of IOLs include monofocal lenses, multifocal IOLs which provide the patient with multiple-focused vision at far and reading distance, and accommodative IOLs which provide the patient with visual accommodation. The flexible nature of many IOLs enables them to be rolled and/or folded up for insertion into the lens capsule.

The removal of the opacified natural crystalline lens and replacement with a lens replacement material, such as an IOL, presently employs a capsulorhexis and/or a capsulotomy procedure. A capsulorhexis generally includes of the removal of a part of the anterior lens capsule and the creation of a hole or opening in the lens capsule, which results, at least in part, from a tearing action. A capsulotomy generally includes of a cutting of the lens capsule, without or with minimum tearing of the lens capsule. Thus, to remove the opacified natural lens material, the lens capsule is opened. There are several known techniques for performing a capsulorhexis and a capsulotomy, including the use of a Fugo plasma blade.

Recently laser systems and methods for treating of cataracts, presbyopia, performing capsulotomies, and for the sectioning and removal of natural crystalline lens material have been developed and introduced. Examples of such innovative and novel systems and methods are found in commonly assigned published patent applications US2007/0173794, US2007/0173795, US 2007/0185475, US 2010/0004641, US 2010/0004643, US 2010/0022994, US 2010/002995, US 2010/0042079, WO 2007/084627, and WO 2007/084694, the entire disclosures of each of which are incorporated herein by reference. Further examples of such innovative and novel systems and methods are found in commonly assigned U.S. patent application Ser. Nos. 12/840,818, 12/831,859, 12/831, 845, 12/831,783 and 12/842,870, the entire disclosures of each of which are incorporated herein by reference.

In the treatment of cataracts, presbyopia, conditions of the eye, and afflictions of the eye, and in particular, in using lasers for such treatments, the determination of the position (relative to other structures of the eye and/or relative to any treatment equipment, such as a laser), and the shape of the structures of the eye is essential to allow the precise application of laser energy to effect the treatment. In general, greater accuracy and precision in making such determinations is beneficial. Further, visual images of these structures for the treating physician to observe can be beneficial and can enhance the outcome of any procedures. Accordingly, as provided in detail in this specification, improvements in the illumination of structures of the eye are provided herein, which improvements give rise to improved determination of the position and shape of structures within the eye, as well as, enhanced images of those structures.

SUMMARY

It is desirable to have systems and methods that would provide enhanced images of the structures of the eye and that would provide for the position and shape of those structures. The present invention, among other things, solves these needs by providing controlled light beam illumination of such structures. Thus, there is provided herein systems and methods for the enhanced illumination of the structures of the eye and for the capture of single composite images of those structures having optimal illumination for each structure.

It is further desirable that the image capture device be well calibrated to permit dimensionally accurate images of the structures of the eye. Such calibration is desirable to eliminate sources of image distortion such as the tilt between the angle of illumination beam and the image plane of the image capture device used to form composite images of the structures of the eye or optical aberrations in the image capture device. Such sources of image distortion are common in imaging applications requiring a large depth of field, such as the present application in imaging the structures of the eye.

Thus, there is provided a method for enhancing the illumination of components of a multi-component structure, the method including: selecting a first predetermined illumination light scan pattern, having a predetermined rate and scan region; selecting a second predetermined illumination light scan pattern, having a predetermined rate and scan region; wherein, at least one of the second scan rate or area is different from the first scan rate or scan region; directing an illuminating light beam in the first scan pattern toward a first component of the multi-component structure, whereby a first illuminated image is created; directing an illuminating light beam in the second scan pattern toward a second component of the multi-component structure, whereby a second illumination image is created; digitally capturing the first illumination image on a first predetermined portion of an image capture device; digitally capturing the second illumination image on a second predetermined portion of the image capture device, wherein the second portion is different than the first portion; thus a single composite image of the illuminated components is created by the image capture device without need for registration of the first to the second illumination image.

There is further provided the forgoing method in which at least one of the predetermined illumination light scan patterns is optimized for the component to be scanned; the first component is the cornea of an eye; the first component is the natural crystalline lens of any eye; and/or the second component is the natural crystalline lens of the eye.

There is further provided a method to calibrate the image capture device so that there exists a known relationship or mapping between each point in the three dimensional volume of space containing the components of interest in the eye and the two dimensional image plane of the image capture device. The method includes a means to present one or more calibration targets to the image capture device, before (or after) use of the image capture device to generate images of structures in the eye, such calibration targets together include a three dimensional array or series of a plurality of uniquely identifiable objects with known positions in the volume of space in which the eye will be imaged. The method further includes means to capture one or more images of the calibration target(s) with the image capture device and identify some or all of the uniquely identifiable objects in the captured image(s) and to record the positions, within the captured image(s), of some or all of the uniquely identifiable objects. Further, the method includes a means to determine a linear or non-linear mathematical relationship or mapping between the known positions of the uniquely identifiable objects in the calibration target(s) and the recorded positions of the uniquely identifiable objects in the captured image(s). Still further, the method includes means to use the foregoing mapping to reduce or eliminate sources of image distortion in the image capture device or inherent in the geometrical arrangement of the image capture device with respect to the volume of space in which the object to be imaged, for example, structures within the eye or calibration target(s) and so be generate an image which is substantially dimensionally accurate. By dimensionally accurate is meant that the distances between entities, such as eye structures or parts of eye structures, in the image captured by the image capture device are substantially the same as corresponding distances between the same entities in the actual object being imaged, except for a single overall scale factor.

Yet further, there is provided a system for providing enhanced illumination of the components of a multi-component structure, the system having: an illumination source for providing an illumination beam; a scanner optically associated with the illumination light source for scanning the illumination beam; a control system, associated with the light source and scanner; the control system including: a first predetermined illumination beam scan pattern, having a predetermined rate and scan region; a second predetermined illumination scan pattern, having a predetermined rate and scan region; wherein, at least one of the second scan rate or region is different from the first scan rate or region; means for digitally capturing a first image generated by the first illuminating beam scan pattern; means for digitally capturing a second image generated by the second illuminating laser beam scan pattern; and, the means for digitally capturing the first image and the means for capturing the second image being different portions of the same means.

Additionally, there is provided a system for the enhanced illumination of the structures of the eye, the system having: an illumination source for providing an illumination beam; a scanner optically associated with the illumination source for scanning the illumination beam; a control system, associated with the illumination source and scanner; the control system including: a first predetermined illumination scan pattern, having a predetermined rate and scan region; a second predetermined illumination scan pattern, having a predetermined rate and scan region; wherein, at least one of the second scan rate or region is different from the first scan rate or area; region for digitally capturing a first image generated by the first illuminating beam scan pattern; means for digitally capturing a second image generated by the second illuminating beam scan pattern; and the means for digitally capturing the first image and the means for capturing the second image being different portions of the same means.

Yet further there is provided a method for enhancing the illumination of the structures of the eye, the method including: scanning an illumination beam in a predetermined rate and scan region over an area of a cornea of an eye; and, scanning the illumination beam at a predetermined rate and area over an area of a lens of the eye; wherein the illumination of the cornea is different from the illumination of the lens. This method may further be such that the illumination of the cornea and the lens are respectively optimal.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

Figure 1A:
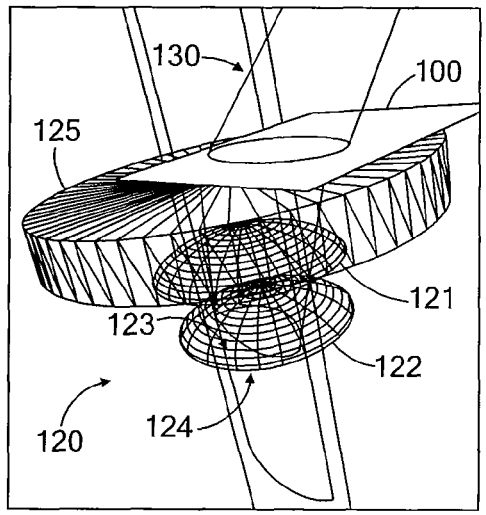
FIGS. 1A to 1D are four different perspective illustrations of the same laser scanning illumination of the structures of the eye of the present invention.
Figure 1B:
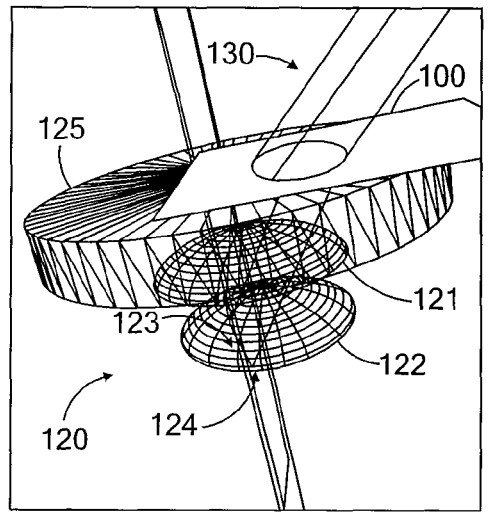
Figure 1C:
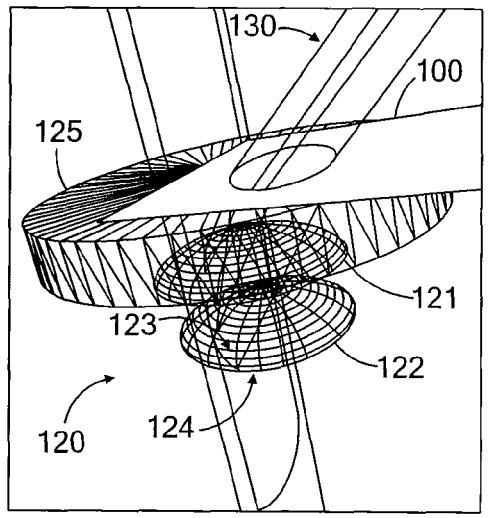
Figure 1D:
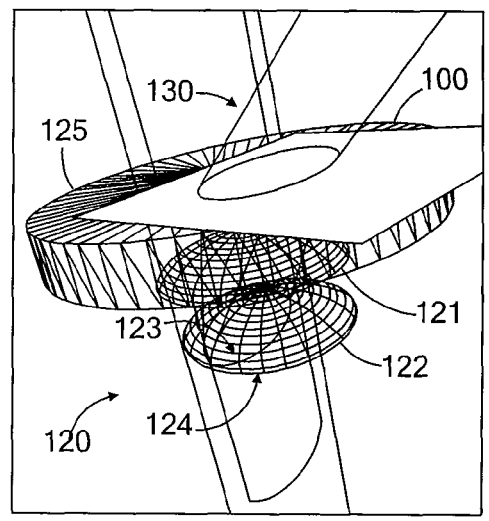

In general, the present inventions relates to methods and systems for providing enhanced laser scan illumination of the eye to provide for improved images of the structures of the eye, and in particular, the cornea and the natural crystalline lens. The present invention further relates to systems and methods utilizing the enhanced laser scan illumination for determining the shape and position of the cornea and the lens and to provide enhanced images of those structures.

In general, the present invention uses a light beam and scanner to illuminate the structures of the eye. The light beam can be generated by a non-coherent light source or a laser source. Examples of laser beam and scanner systems that can be used for illumination are disclosed in US 2007/0173794, US 2007/0173795, US 2007/0185475, US 2010/0004641, US 2010/0004643, US 2010/0022994, US 2010/002995, US 2010/0042079, WO 2007/084627, and WO 2007/084694. Further examples of such laser beam and scanner systems are found in commonly assigned U.S. patent application Ser. Nos. 12/840,818, 12/831,859, 12/831,845, 12/831,783 and 12/842,870. In the case of using a laser source, the illumination laser should be an eye safe laser. Thus, the illumination laser could be a laser that is deferent from the therapeutic laser, or it could be the therapeutic laser, but at a power level that is below the threshold where the laser can affect the structures that are illuminated. In the case of using a non-coherent light source, the laser beam and scanner systems disclosed in the previously mentioned US 2007/0173794, US 2007/0173795, US 2007/0185475, US2010/0004641, US 2010/0004643, US 2010/0022994, US 2010/002995, US2010/0042079, WO 2007/084627, WO 2007/084694, U.S. patent application Ser. Nos. 12/840,818, 12/831,859, 12/831,845, 12/831,783 and 12/842,870 can be adapted to include such a non-coherent light source for illumination instead of a laser source.

In conventional illumination techniques, which illuminate all of the structures at once and capture an image of these illuminated structures for example with a digital camera; the images of the eye are over or under exposed in different areas and on different structures. Thus, with these conventional techniques it is believed that in general evenly illuminated clear and sharp images of multiple structures of the eye, in a single image, are difficult to obtain, if not unobtainable. Instead, such conventional images have over exposed or underexposed areas resulting in bright and dark spots that detrimentally affect the clarity and sharpness of the overall image. These detrimental effects are in part due to the different structures of the eye responding differently to the illumination light. Thus, illumination light that is best to capture, for example, an image of the anterior surface of the lens, may not be best to capture a peripheral edge of the cornea. However, in such "one illumination source fits" all type of techniques there no way, or at a minimum it is exceeding difficult, to tailor the illumination to all of the structures of the eye in a single image.

To solve these drawbacks of conventional illumination and image capture systems, the present inventions scan an illumination beam of light on the structures of the eye to be illuminated. The scan rate and scan area are predetermined based upon the structure of the eye to be illuminated, the section of that structure to be illuminated, and the relative location and size of the pupil. As the illumination beam of light is scanned along a section of a particular structure of the eye to be illuminated, the illuminated images from that scan are captured by predetermined pixels, or lines, on an image capture device, such as a digital camera. As additional structures in the eye are scanned, other predetermined pixels, or lines on the digital camera capture their illuminated images. In this way, a composite image, based upon each individual scan of each individual structure, of the illuminated structures of the eye is built, with each structure having the optimal illumination. Thus, the present system provides the ability to have predetermined and preselected multiple and varied illuminations of components parts, sub-structures, or structures of a multi-component structure, such as the human eye, and to create a single, clear and sharp image of all of those components in the multi-component structure. The images can be created real-time in a single procedure (serial collection of a plurality of illumination scans) without the need for subsequent or later digital alteration or digital enhancement of the images, such as by using software sold under the trademark PHOTOSHOP. Thus, for example in the present system and method the size of the pupil is determined. The scanning of light on a particular area of the cornea is performed. The scan preferably is from about 12-13 mm in length and at a rate that properly, and preferably optimally, illuminates the cornea based upon the setting of the camera. The illuminated images from this first scan would be for example captured by pixels at for example lines X to X+250 of the camera. The scan of a particular area of the anterior surface of the lens of the eye would then be performed (preferably the areas are directly anterior to the area of the cornea and thus a cross-section of the structures is obtained). To avoid interference from the pupil, this scan is from about 7 to 7.5 mm and at a rate that properly, and preferably optimally, illuminates the anterior capsule of the lens based upon the setting of the camera. The illuminated images for this second scan would be for example captured by pixels at for example lines X+252 to X+300. In this way both the scanned images of the cornea and the anterior capsule of the lens would be captured in a single image, with each having different and optimal illumination. The steps of scanning, and capturing images on further lines of the camera would be continued until all of the desired structures of the eye have been captured in a single image. Further, it should be understood, that the order of scans and the location of capture on the lines of the camera may vary for different applications. In addition, the light beam used in the scan can be generated by a laser or by a super luminescent diode (SLD). Use of an SLD is beneficial in that it is a non-coherent source that avoids laser speckle which degrades the image quality.

Turning to FIGS. 1A to 1D, there are four views from different perspectives of the images of scans of the illuminating light to create single composite images 100 of areas of the structures of the eye 120. Thus, in these figures there is shown a cornea 121 and a natural crystalline lens 122, which has an anterior capsule 123 and a posterior capsule 124. There is also shown an image window 125, which may be of the illumination system, such as a part of a patient interface. In these figures there are shown ray lines 130 signifying the scanned illumination light beam used to illuminate the structures of the eye. As can be seen from the image position 100, these figures show different perspective views of the same scans, image, and eye structures, but from different views (e.g., 12, 3, 6 and 9 o'clock if one were to use the face of a clock as a reference).

Figure 2:
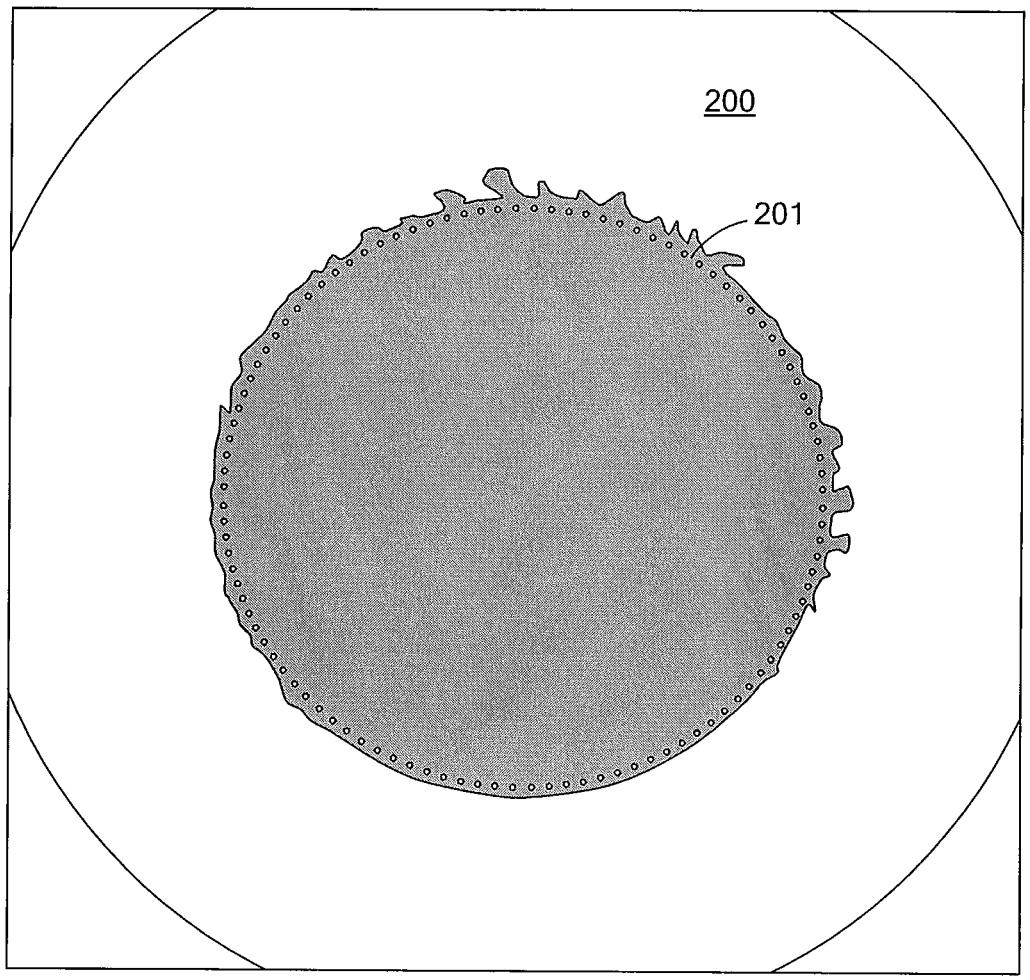
FIG. 2 is a diagram of a pupil of an eye.

FIG. 2 shows a section of an eye 200, with a computer generated line 201 positioned concentrically with the edge of the pupil. This line 201 can be used to determine the diameter of the dilated pupil, which diameter may then be used to determine and optimize the length of a particular illumination scan of structures that are positioned posterior to the pupil.

Figure 3:
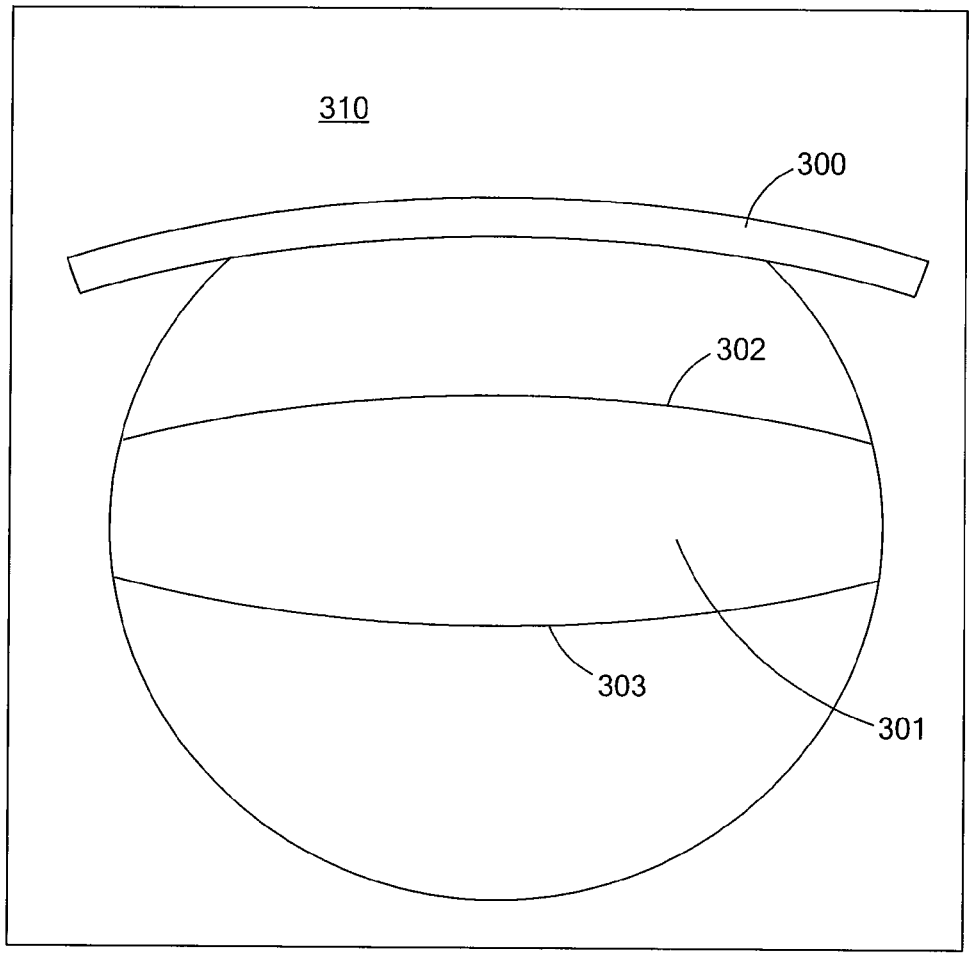
FIGS. 3 to 5 are single composite images of the eye obtained by the present invention.
Figure 4:
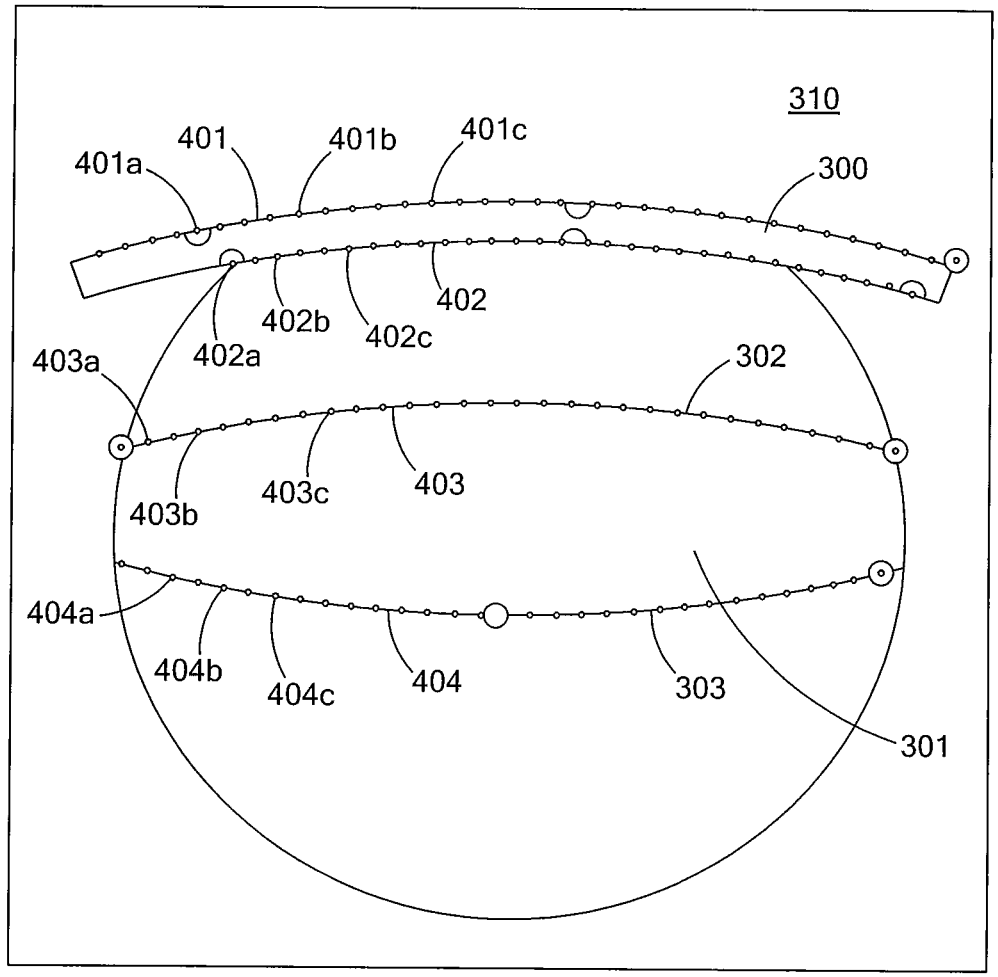
Figure 5:
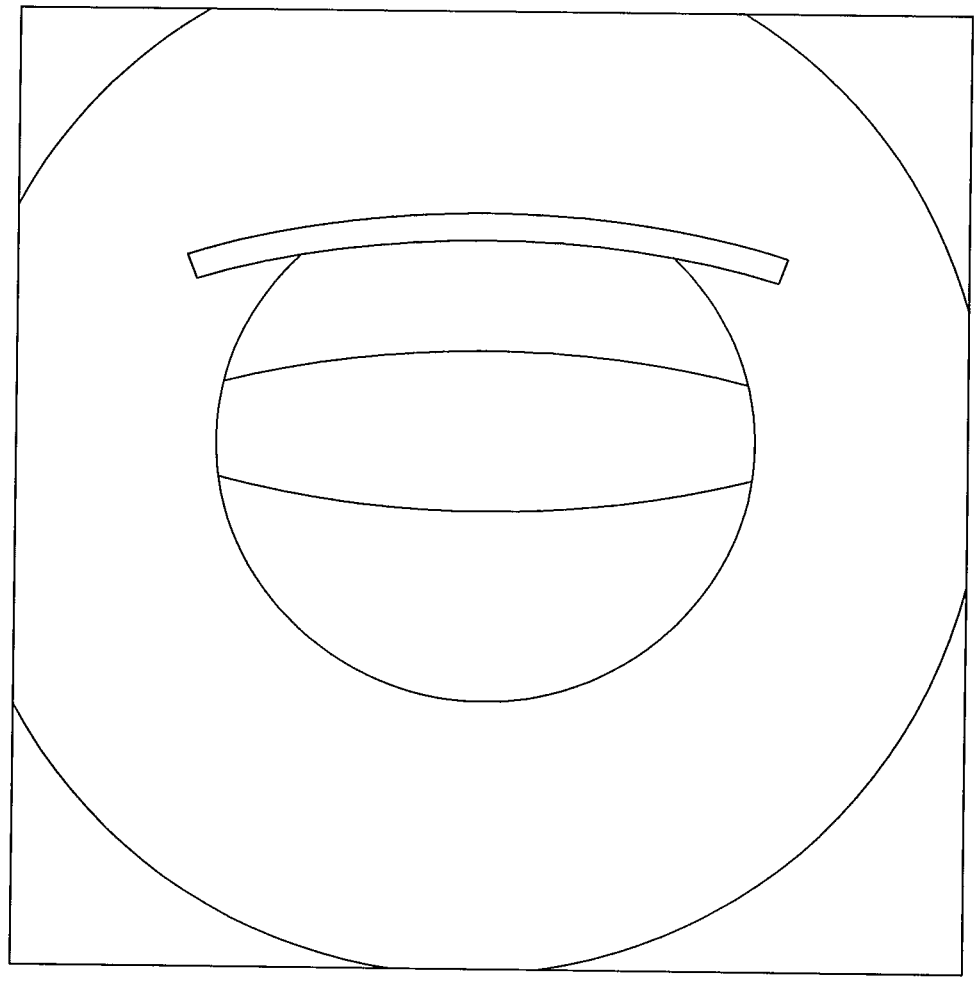
Figure 6:
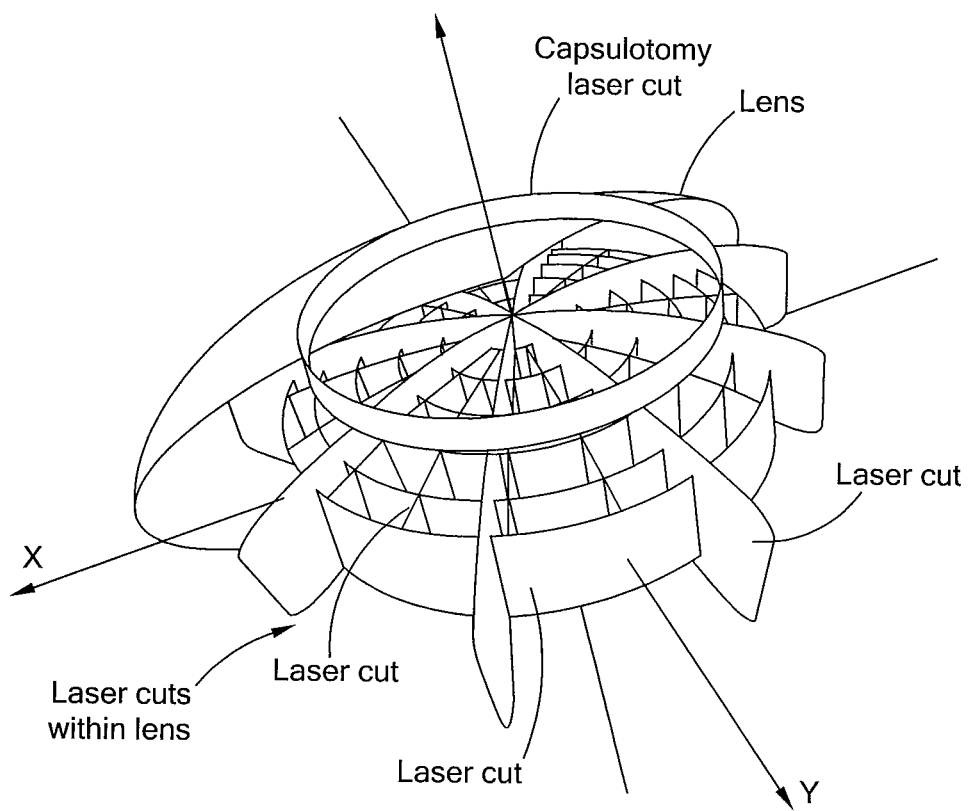
FIG. 6 is an illustration of a therapeutic laser shot pattern that can be directed toward the eye based upon the enhanced images obtained by the present inventions.

FIG. 3 provides a single image 310 of the structures of the eye that was taken using scanned light illumination, which each scan having a different scan rate and scan area, which rates and areas were predetermined to optimize the images obtained. Thus, there is shown the cornea 300, the lens 301, and the lens anterior capful 302 and posterior capsule 303. Turning to FIG. 4 there is shown the same image 310 of FIG. 3 to which position and shape determination lines have been added via computer. Thus, line 401 follows the anterior surface of the cornea and has a plurality of points, of which points 401a, 401b and 401c are numbered for purposes of illustration and simplification of the drawing. Line 402 follows the posterior surface of the cornea and has a plurality of points, of which points 402*a*, 402*b* and 402*c* are numbered for purposes of illustration and simplification of the drawing. Line 403 follows the anterior lens capsule and has a plurality of points, of which points 403*a*, 403*b* and 403*c* are numbered for purposes of illustration and simplification of the drawing. Line 404 follows the posterior lens capsule and has a plurality of points, of which points 404*a*, 404*b* and 404*c* are numbered for purposes of illustration and simplification of the drawing. These various computer generated points and lines, which are generated based upon the enhanced image obtained from the light scan illumination, are used to determine the position and shape of the lens and cornea. This position and shape information can then be used to determine a shot pattern for the therapeutic laser such as the shot patterns shown in FIG. 6.

The scanned illumination techniques have the ability to obtain clear and sharp images of the peripheral edges of the cornea, i.e., the outer section of the cornea that is still clear but which is adjacent the sclera. Obtain clear images of this portion of the cornea, as well as obtaining precise position and shape of this section of the cornea is beneficial, for example during cataract surgery. It is this section of the eye that the incision is made to provide access to the lens. Because this area of the cornea is clear it is difficult for convention technology, such as OCT, to obtain the clarity and sharpness of images necessary to precisely determine the position and shape of this area. In addition, the scanned illumination techniques enhance details in the anterior and posterior capsules and enables imaging of posterior capsule through dense cataracts.

Figure 7A:
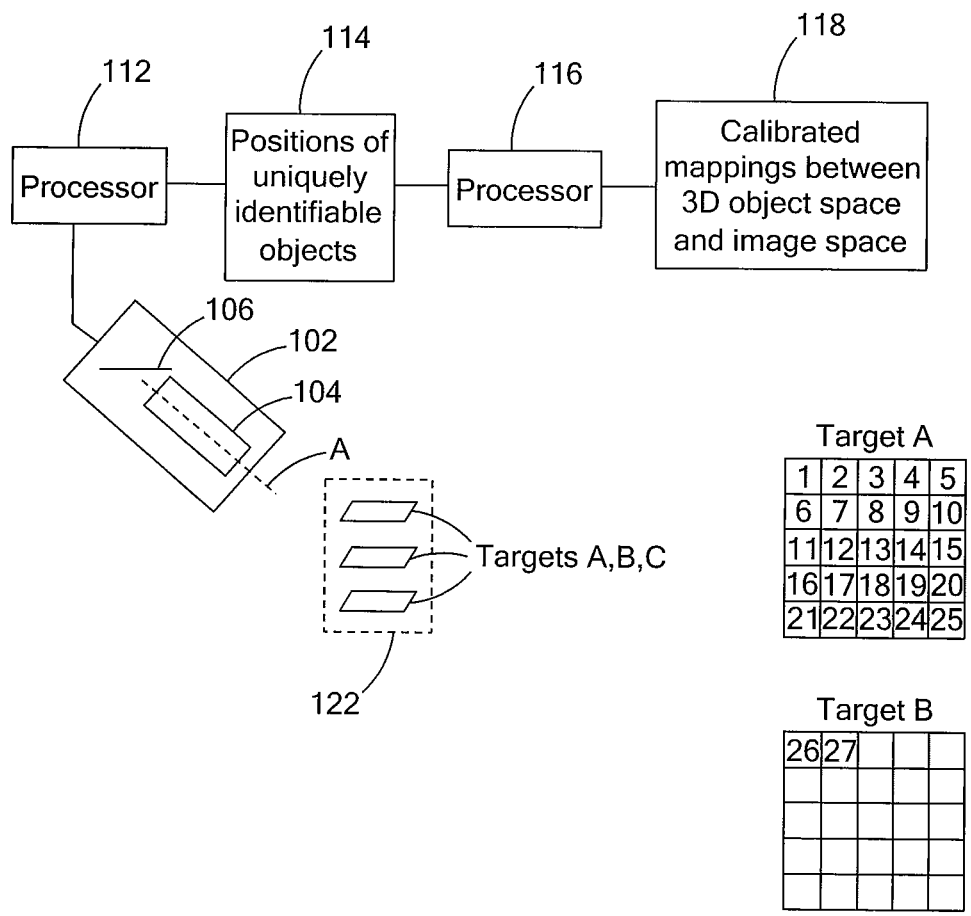
FIG. 7A schematically shows a portion of a system for calibrating images of an object, such as an eye, in accordance with the present invention.
Figure 7B:
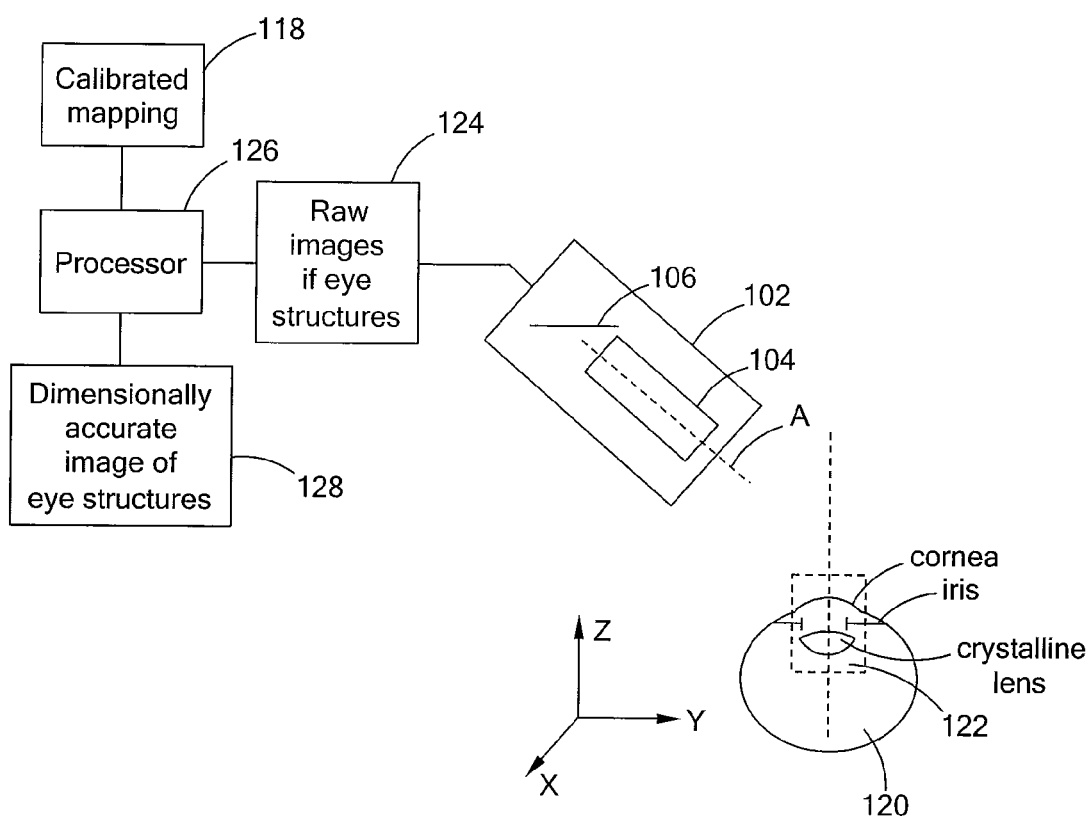
FIG. 7B schematically shows a second portion of the system of FIG. 7A in accordance with the present invention.

In order to correct for images generated in the systems and methods described previously with respect to FIGS. 1-6, a calibration procedure can be employed. As shown in FIGS. 7A-B, the calibration system 100 includes an image capture device 102, such as a camera, that including an image forming lens 104 and a planar detector 106 that has its plane angled relative to the optic axis A of the lens 104. An image receiving aperture 108 is aimed at an object volume 110, which contains the object of which the image capture device 102 forms an image. Such an arrangement, with an appropriately selected angle between the optic axis A of the lens 104 and the plane of the detector 106, allows the image capture device 102 to form an image with a large depth of focus in the z direction, which is aligned with the optic axis of the crystalline lens of an eye 120 as shown in FIG. 7B.

Referring to FIG. 7A, to calibrate the system, one or more targets, containing uniquely identifiable objects, such as squares 1, 2, . . . , are presented to the image capture device 102, usually sequentially. The targets are carefully made and are placed in exactly known positions. One example of such uniquely identifiable objects is ARTags as described in "Augmented Reality Tags", Augmented Reality: A Practical Guide, Stephen Cawood and Mark Fiala.

One or more images are generated for each target. The images formed at planar detector 106 are sent to processor 112, wherein processor 112 analyzes each image and identifies some or all of the uniquely identifiable objects in the image and records the positions of the uniquely identifiable objects in a memory 114. The recorded positions are then sent to processor 116, which generates a linear or non-linear mathematical relationship or mapping between the positions of the uniquely identifiable objects in the images of the targets and the accurately known positions of the uniquely identifiable objects within the object volume. An example of such a mapping is the TSAI algorithm. R. Y. Tsai, *An Efficient and Accurate Camera Calibration Technique for 3D Machine Vision*, Proceedings of IEEE Conference on Computer Vision and Pattern Recognition, Miami Beach, Fla. ,pp. 364-374, 1986.

The mapping is stored in memory 118 and is used to correct raw images generated by the image capture device to create dimensionally accurate images of the objects within the object volume. The use of uniquely identifiable objects greatly simplifies the process of generating the mathematical mapping required to create dimensionally accurate images.

The mapping determined above is used to process raw images of the structures within the eye, for example, surfaces and other features of the cornea and crystalline lens; c.f. FIG. 7B. As shown in FIG. 7B, the image capture device 102 forms raw images of the structures within the eye 120, which are situated in the object volume 122 and which are illuminated by a plane of light B which illuminates a longitudinal section of the eye 120. In FIG. 7B, the longitudinal section is perpendicular to the plane of the page. The raw images of the illuminated longitudinal section are subject to various sources of distortion including: the viewing angle between the optic axis of image capture device lens and the z axis, angle of the detector plane to the optic axis of the lens and optical aberrations in the image capture device lens. Accordingly, the raw images of the object volume 122 are stored in memory 124 and sent to processor 126. Using the calibrated mathematical mapping from memory 118, the processor 126 processes the raw images received from memory 124 to form substantially dimensionally accurate images of the eye that are stored in memory 128.

In other words, distances between structures or parts of structures measured on the processed images correspond, except for an overall scale factor to the corresponding distances in the illuminated longitudinal section of the eye.

The dimensionally accurate images allow the application of laser energy used in the treatment of cataracts to be accurately applied to specific areas within the eye, for example to cut a capsulotomy or to fragment the crystalline lens into pieces for easier removal in a cataract procedure.

With the above mentioned discussion of improved illumination and calibration, it is envisioned that such techniques could be applied to various imaging and beam placement systems. One example of such a system is presented herewith. For example, it is envisioned to apply the improved illumination and calibration to a system that uses a confocal system where the imaging and beam delivery systems are coaxial and share a common focus and optical pathway. Such a system would have no systematic errors between the imaging of the eye and the delivery of laser shots, such as femtosecond pulses. The imaging system could be based on the Scheimpflug principle so that a single image from the anterior cornea to the posterior capsule is captured resulting in enhanced depth of field. The scanning laser being such that it enhances contrast at important interfaces and, thus allows for anterior and posterior capsule-fragments to be closer to the posterior place due to the more accurate beam placement due to the present invention. A scanning beam camera and optics would be used to provide a high contrast to noise ratio. Such an imaging system would use three-dimensional reconstruction from ray tracing and so avoids two-dimensional stitching of multiple scans.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A method for enhancing the illumination of components of a multi-component structure, the method comprising:

a. selecting a first predetermined illumination laser scan pattern, having a predetermined rate and area;
b. selecting a second predetermined illumination laser scan pattern, having a predetermined rate and area; wherein, at least one of the second scan rate or area is different from the first scan rate or area;
c. directing a first illuminating beam of light in the first scan pattern toward a first component of the multi-component structure, whereby a first illuminated image is created;
d. directing a second illuminating beam of light in the second scan pattern toward a second component of the multi-component structure, whereby a second illumination image is created;
e. digitally capturing the first illumination image on a first predetermined portion of an image capture device;
f. digitally capturing the second illumination image on a second predetermined portion of the image capture device, wherein the second portion is different than the first portion;
g. whereby a single composite image of the illuminated components is created by the image capture device.

2. The method of claim 1, wherein at least one of the predetermined illumination laser scan patterns is optimized for the component to be scanned.

3. The method of claim 1, wherein the first component is the cornea of an eye.

4. The method of claim 1, wherein the first component is the natural crystalline lens of any eye.

5. The method of claim 3 wherein the second component is the natural crystalline lens of the eye.

6. A system for providing enhanced the illumination of the components of a multi-component structure, the system comprising:
   a. an illumination light source for providing an illumination laser beam;
   b. a scanner optically associated with the illumination light source for scanning the illumination beam;
   c. a control system, associated with the illumination light source and scanner; the control system having a structure to control the illumination light source and the scanner so that the following scan patterns are generated:
      1. a first predetermined illumination light scan pattern, having a predetermined rate and area;
      2. a second predetermined illumination light scan pattern, having a predetermined rate and area; wherein, at least one of the second scan rate or area is different from the first scan rate or area; and
   the system further comprising:
   d. means for digitally capturing a first image generated by the first illumination light beam scan pattern;
   e. means for digitally capturing a second image generated by the second illumination light beam scan pattern; and,
   f. the means for digitally capturing the first image and the means for capturing the second image being different portions of the same means.

7. A system for providing enhanced the illumination of the structures of the eye, the system comprising:
   a. an illumination light source for providing an illumination light beam;
   b. a scanner optically associated with the illumination light source for scanning the illumination light beam;
   c. a control system, associated with the illumination light source and scanner; the control system having a structure to control the illumination light source and the scanner so that the following scan patterns are generated:
      1. a first predetermined illumination light scan pattern, having a predetermined rate and area;
      2. a second predetermined illumination light scan pattern, having a predetermined rate and area; wherein, at least one of the second scan rate or area is different from the first scan rate or area; and
   the system further comprising:
   d. means for digitally capturing a first image generated by the first illuminating light beam scan pattern;
   e. means for digitally capturing a second image generated by the second illuminating light beam scan pattern; and,
   f. the means for digitally capturing the first image and the means for capturing the second image being different portions of the same means.

8. A method for enhancing the illumination of the structures of the eye, the method comprising:
   scanning an illumination light beam in a predetermined rate and area over an area of a cornea of an eye; and,
   scanning the illumination light beam in a predetermined rate and area over an area of a lens of the eye; wherein the illumination of the cornea is different from the illumination of the lens.

9. The method of claim 8, wherein the illumination of the cornea and the lens are respectively optimal.

* * * * *